United States Patent
De Nanteuil et al.

(10) Patent No.: US 7,442,692 B2
(45) Date of Patent: Oct. 28, 2008

(54) INDANYL-PIPERAZINE COMPOUNDS

(75) Inventors: Guillaume De Nanteuil, Suresnes (FR); Bernard Portevin, Elancourt (FR); Philippe Gloanec, Marly-le-Roi (FR); Mark Millan, Le Pecq (FR); Jean-Claude Ortuno, Bois-d'Arcy (FR); Clotilde Mannoury La Cour, Paris (FR); Alain Gobert, Rueil-Malmaison (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 265 days.

(21) Appl. No.: 11/391,916

(22) Filed: Mar. 29, 2006

(65) Prior Publication Data
US 2006/0223830 A1    Oct. 5, 2006

(30) Foreign Application Priority Data
Mar. 30, 2005    (FR)    ................................... 05.03071

(51) Int. Cl.
| | |
|---|---|
| A61K 31/551 | (2006.01) |
| A61K 31/495 | (2006.01) |
| A61K 31/496 | (2006.01) |
| C07D 295/084 | (2006.01) |
| C07D 295/125 | (2006.01) |
| C07D 295/145 | (2006.01) |

(52) U.S. Cl. ............. 514/218; 514/255.03; 514/252.13; 514/253.01; 540/575; 544/360; 544/379; 544/398; 544/399; 544/400; 544/402

(58) Field of Classification Search ........................ None
See application file for complete search history.

(56) References Cited

FOREIGN PATENT DOCUMENTS

| EP | 0745597 | 12/1996 |
|---|---|---|
| WO | 92/10192 | 6/1992 |
| WO | 2004/042351 | 5/2004 |

OTHER PUBLICATIONS

Ryckmans et al. Bioorganic & Medicinal Chemistry Letters, vol. 12, pp. 3195-3198 (2002).*
Preliminary Search Report: FR 0503071—Oct. 26, 2005.
* cited by examiner

*Primary Examiner*—Emily Bernhardt
(74) *Attorney, Agent, or Firm*—Hueschen and Sage

(57) ABSTRACT

A compound selected from those of formula (I):

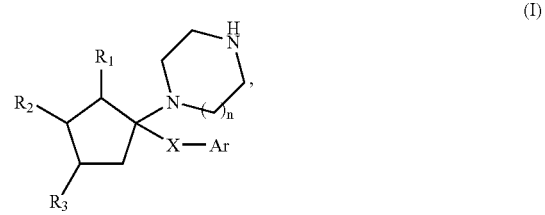

wherein:
  $R_3$ represents a hydrogen atom, and $R_1$ and $R_2$ together with the carbon atoms carrying them form a benzene, naphthalene or quinoline ring structure, each of the ring structures being optionally substituted,
  or $R_1$ represents a hydrogen atom, and $R_2$ and $R_3$ together with the carbon atoms carrying them form a benzene, naphthalene or quinoline ring structure, each of the ring structures being optionally substituted,
  n represents 1 or 2,
  —X— represents a group selected from —$(CH_2)_m$—O—Ak-, —$(CH_2)_m$—$NR_4$-Ak-, —(CO)—$NR_4$-Ak- and —$(CH_2)_m$—$NR_4$-(CO)—,
  m represents an integer between 1 and 6 inclusive, Ak represents an optionally substituted alkylene chain, and $R_4$ represents a hydrogen atom or an alkyl group,
  Ar represents an aryl or heteroaryl group,
its enantiomers, diastereoisomers, and addition salts thereof with a pharmaceutically acceptable acid.

Medical products containing the same which are useful in the treatment of conditions requiring a serotonin reuptake inhibitor and/or $NK_1$ antagonist.

8 Claims, No Drawings

INDANYL-PIPERAZINE COMPOUNDS

The present invention relates to indanyl-piperazine compounds, to a process for their preparation and to pharmaceutical compositions containing them, and also to their use as serotonin reuptake inhibitors and $NK_1$ antagonists.

The compounds of the present invention act as serotonin reuptake inhibitors.

By virtue of that fact, they are useful in the treatment of depressive states (Goodnick and Goldstein, *J Psychopharmacol* 1998, 12 (Suppl B):S55-S87; Cheer and Goa, *Drugs* 2001, 61:81-110; MacQueen et al., *CNS Drug Rev* 2001, 7:1-24; Wagstaff et al., *Drugs* 2002, 62:655-703), anxiety states such as generalised anxiety, panic attacks and phobias (Feighner, *J Clin Psychiatry* 1999, 60 (Suppl 22): 18-22; Bakker et al., *Int clin Psychopharmacol* 2000, 15 (Suppl 2):S25-S30; Davidson, *Int Clin Psychopharmacol* 2000, 15 (suppl 1):S13-S17; Schneier, *J Clin Psychiatry* 2001, 62 (Suppl 1):43-48), the harmful effect of stress whether psychological (Marona-Lewicka and Nichols, *Stress* 1997, 2:91-100; Mar et al., *Pharmacol Biochem Behav* 2002, 73:703-712; Will et al., *Mol Psychiatry* 2003, 8:925-932; Ballenger, *J Clin Psychiatry* 2004, 65:1696-1707) or neurotoxic (Malberg and Duman, *Neuropsychopharmacology* 2003, 28:1562-1571; Santarelli et al., *Science* 2003, 301:805-809; Czeh et al., *Neuropsychopharmacology* 2005, 30:67-79; Malberg and Schechter, *Curr Pharm Des* 2005, 11:145-155), impulsive states such as "ODC" or obsessive-compulsive behaviour disorders (Njung'e and Handley, *Br J Pharmacol* 1991, 104:105-112; Ichimaru et al., *Jpn J Pharmacol* 1995, 68:65-70; Pigott and Seay, *J Clin Psychiatry* 1999, 60:101-106; Vythilingum et al., *Int Clin Psychopharmacol* 2000, 15 (Suppl 2)S7-S13), aggressive states (Knutson et al., *Am J Psychiatry* 1998, 155: 373-379; Lanctot et al., *Neuropsychopharmacology* 2002, 27:646-654; New et al., *Psychopharmacology* 2004, 176: 451-458), obesity and appetite disorders such as bulimia (Proietto et al., *Expert Opin Investig Drugs* 2000, 9:1317-1326; Ljung et al., *J Intern Med* 2001, 250:219-224; Appolinario et al., *CNS Drugs* 2004, 18:629-651; Appolinario and McElroy, *Curr Drug Targets* 2004, 5:301-307), pain states (Aragona et al., *Eur J Pain* 2005, 9:33-38; Millan et al., *Neuropharmacology* 2002, 42:677-684; Duman et al., *J Pharmacol Sci* 2004, 94:161-165; Otsuka et al., *J Anesth* 2004, 15:154-158); and, in relation to those entities, disorders of behaviour and of neuronal degeneration associated with dementia and other disorders of aging (Lyketos et al., *Am J Psychiatry* 2000, 157:1686-1689; Lanctot et al., *J Neuropsychiatry Clin Neurosci* 2001, 13:5-21; Lanctot et al., *Neuropsychopharmacology* 2002, 27:646-654; Pollock et al., *Am J Psychiatry* 2002, 159:460-465).

Furthermore, the compounds of the present invention are also active as neurokinin $NK_1$ antagonists.

By virtue of that fact, they are also useful in the treatment of depressive states (Rupniak et al., *Behav Pharmacol* 2001, 12:497-508; Rupniak et al., *Neuropharmacology* 2003, 44:516-523; Kramer et al., *Neuropsychopharmacology* 2004, 29:385-392; Dableh et al., *Eur J Pharmacol* 2005, 507:99-105), anxiety states such as generalised anxiety, panic attacks and phobias (Rupniak et al, *Behav Pharmacol* 2001, 12:497-508; Santarelli et al., *Proc Natl Acad Sci USA* 2001, 98:1912-1927; Varty et al., *Neuropsychopharmacology* 2002, 27:371-379; Rupniak and Kramer, *Neuropsychopharmacology* 2002, 13:169-177), the harmful effect of stress whether psychological (Ballard et al., *Eur J Pharmacol* 2001, 412:255-264; Rupniak and Kramer, *Neuropsychopharmacology* 2002, 13:169-177; Spooren et al., *Eur J Pharmacol* 2002, 435:161-170; Steinberg et al., *J Pharmacol Exp Ther* 2002, 303:1180-1188) or neurotoxic (Van der Hart et al., *Mol Psychiatry* 2002, 7:933-941; Morcuende et al., *Eur J Neurosci* 2003, 18:1828-1836; Guest et al., *Brain Res* 2004, 1002:1-10; Czeh et al., *Neuropsychopharmacology* 2005, 30:67-79), impulsive states such as obsessive-compulsive behaviour disorders (Culman et al., *Br J Pharmacol* 1995, 114:1310-1316; Tschöpe et al., *Br J Pharmacol* 1992, 107:750-755; Rupniak et al., *Behav Pharmacol* 2001, 12:497-508; Millan et al., *Neuropharmacology* 2002, 42:677-684), aggressive states (Siegel and Schubert, *Rev Neurosci* 1995, 6:47-61; De Felipe et al., *Nature* 1998, 392:394-397; Rupniak et al., *Behav Pharmacol* 2001, 12:497-508), but also drug abuse (Murtra et al., *Nature* 2000, 405:180-183; Ripley et al., *Neuropharmacology* 2002, 43:1258-1268; Gadd et al., *J Neurosci* 2003, 23:8271-8280), psychotic states (Zachrisson et al., *Eur Neuropsychopharmacol* 2000, 10:355-363) and extrapyramidal motor effects caused by antipsychotics (Anderson et al., *J Pharmacol Exp Ther* 1995, 274:928-936, Steinberg et al., *J Pharmacol Exp Ther* 2002, 303:1180-1188), sexual dysfunctions (Priest et al., *Brain Res Mol Brain Res* 1995, 28:61-71; Daniels et al., *Neurosci Lett* 2003, 338:111-114; Kramer et al., *Science* 1998, 281:1640-1644; Kramer et al., *Neuropsychopharmacology* 2004, 29:385-392), disturbances of chronobiological rhythms such as circadian rhythms (Shibata et al., *Brain Res* 1992, 597:257-263; Challet et al., *Brain Res* 1998, 800:32-39; Challet et al., *Neuropharmacology* 2001, 40:408-415; Gannon et al., *Neuropharmacology*, in press), pain (Seguin et al., *Pain* 1995, 61:325-343; De Felipe et al., *Nature* 1998, 392:394-397; Sanger, *Br J Pharmacol* 2004, 141:1303-1312) and/or inflammation (Seabrook et al., *Eur J Pharmacol* 1996, 317:129-135; Holzer, *Digestion* 1998, 59:269-283; Joos and Pauwels, *Curr Opin Pharmacol* 2001, 1:235-241; Sanger, *Br J Pharmacol* 2004, 141:1303-1312), nausea and other gastrointestinal disorders (McAllister and Pratt *Eur J Pharmacol* 1998, 353:141-148; Gardner et al., *Regulatory Peptides* 1996, 65:45-53; Patel and Lindley, *Expert Opin. Pharmacother* 2003, 4:2279-2296; Sanger, *Br J Pharmacol* 2004, 141:1303-1312); and, in relation to those entities, disorders of behaviour and of neuronal degeneration associated with dementia and other disorders of aging (Raffa, *Neurosci Biobehav Rev* 1998, 22:789-813).

Because the compounds are active both on $NK_1$ receptors and on serotonin (5-HT) reuptake sites, they should have complementary and synergistic mechanisms for controlling impulsive, aggressive, painful and, above all, depressive states. It has moreover been shown that blocking $NK_1$ receptors potentiates the influence of 5-HT reuptake inhibitors on serotoninergic transmission: because of that fact, such compounds should bring about more rapid and more robust antidepressant effects (Guiard et al., *J Neurochem* 2004, 89:54-63; Froger et al., *J Neurosci* 2001, 21:8188-8197). The rapid anxiolytic effects of NK, antagonists should, moreover, be complementary to the anxiolytic effects of 5-HT reuptake inhibitors, which are expressed after long-term treatment. With regard to the anxiogenic effects brought about by 5-HT at the start of treatment (Bagdy et al., *Int J Neuropsychopharmacol* 2001, 4:399-408), these should be prevented by the NK, antagonist properties (Ballard et al., *Eur J Pharmacol* 2001, 412:255-264; Rupniak et al., *Neuropharmacology* 2003, 44:516-523). As far as the other undesirable effects associated with 5-HT reuptake blocking are concerned, such as emetic effects (Goldstein and Goodnick, *J Psychopharmacol* 1998, 12 (Suppl B):S55-S87; Edwards and Anderson, *Drugs* 1999, 57:507-533; Waugh and Goa, *CNS Drugs* 2003, 17:343-362) and the causation of sexual dysfunctions (Goldstein and Goodnick, *J Psychopharmacol* 1998, 12 (Suppl B):S55-S87; Montgomery et al., *J Affect disord* 2002, 69:119-

140; Hirschfeld, *J Clin Psychiatry* 2003, 64 (Suppl 18):20-24), NK$_1$ antagonists should also be capable of counteracting those effects.

Consequently, compounds that are both NK$_1$ antagonists and serotonin reuptake inhibitors should have therapeutic advantages over compounds that interact with only one or other of those two targets.

More specifically, the present invention relates to compounds of formula (I):

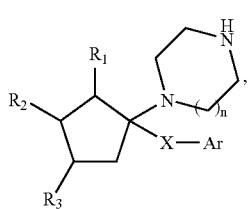

wherein:
  R$_3$ represents a hydrogen atom, and R$_1$ and R$_2$ together with the carbon atoms carrying them form a benzene, naphthalene or quinoline ring structure, preferably a benzene ring, each of those ring structures being optionally substituted by one or more identical or different substituents selected from hydrogen, halogen and linear or branched C$_1$-C$_6$alkyl optionally substituted by one or more halogen atoms,
  or R$_1$ represents a hydrogen atom, and R$_2$ and R$_3$ together with the carbon atoms carrying them form a benzene, naphthalene or quinoline ring structure, preferably a benzene ring, each of those ring structures being optionally substituted by one or more identical or different substituents selected from hydrogen, halogen and linear or branched C$_1$-C$_6$alkyl optionally substituted by one or more halogen atoms,
  n represents 1 or 2,
  —X— represents a group selected from —(CH$_2$)$_m$—O—Ak-, —(CH$_2$)$_m$—NR$_4$-Ak-, —(CO)—NR$_4$-Ak- and —(CH$_2$)$_m$—NR$_4$—(CO)—,
  m represents an integer between 1 and 6 inclusive, Ak represents a linear or branched C$_1$-C$_6$alkylene chain optionally substituted by a hydroxy group, and R$_4$ represents a hydrogen atom or a linear or branched C$_1$-C$_6$alkyl group,
  Ar represents an aryl or heteroaryl group, to their optical isomers, and also to addition salts thereof with a pharmaceutically acceptable acid.

Optical isomers are understood to mean enantiomers and diastereoisomers.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

An aryl group is understood to mean phenyl, biphenylyl or naphthyl, each of those groups being optionally substituted by one or more identical or different groups selected from halogen, linear or branched C$_1$-C$_6$alkyl, linear or branched C$_1$-C$_6$alkoxy, hydroxy, cyano and linear or branched C$_1$-C$_6$trihaloalkyl.

A heteroaryl group is understood to mean an aromatic mono- or bi-cyclic 5- to 12-membered group containing one, two or three hetero atoms selected from oxygen, nitrogen and sulphur, it being understood that the heteroaryl group may be optionally substituted by one or more identical or different groups selected from halogen, linear or branched C$_1$-C$_6$alkyl, linear or branched C$_1$-C$_6$alkoxy, hydroxy and linear or branched C$_1$-C$_6$trihalo-alkyl.

Among the heteroaryl groups there may be mentioned, without implying any limitation, the groups thienyl and pyridyl.

n preferably represents 1.

m preferably represents 1.

Ar preferably represents an aryl group.

Preferred compounds according to the invention are:
1-[(1RS)-1-(3,5-dibromobenzyloxymethyl)indan-1-yl]piperazine, its optical isomers, and also addition salts thereof with a pharmaceutically acceptable acid,
1-[(1RS)-1-(3,5-dimethylbenzyloxymethyl)indan-1-yl]piperazine, its optical isomers, and also addition salts thereof with a pharmaceutically acceptable acid,
1-[2-(3,5-dimethylbenzyloxymethyl)indan-2-yl]piperazine, and also addition salts thereof with a pharmaceutically acceptable acid,
N-[(3,5-bis(trifluoromethyl)benzyl]-2-(1-piperazinyl)-2-indancarboxamide, and also addition salts thereof with a pharmaceutically acceptable acid,
(1RS)-N-benzyl-N-methyl-1-(1-piperazinyl)-1-indancarboxamide, its optical isomers, and also addition salts thereof with a pharmaceutically acceptable acid,
(1RS)-N-[3,5-bis(trifluoromethyl)benzyl]-N-methyl-1-(1-piperazinyl)-1-indancarbox-amide, its optical isomers, and also addition salts thereof with a pharmaceutically acceptable acid,
(1RS)-N-(3,5-dimethylbenzyl)-1-(1-piperazinyl)-1-indancarboxamide, its optical isomers, and also addition salts thereof with a pharmaceutically acceptable acid,
N-(3,5-difluorobenzyl)-2-(1-piperazinyl)-2-indancarboxamide, its optical isomers, and also addition salts thereof with a pharmaceutically acceptable acid,
N-(3,5-dichlorobenzyl)-N-methyl-2-(1-piperazinyl)-2-indancarboxamide, and also addition salts thereof with a pharmaceutically acceptable acid,
(1RS)-N-(3,5-difluorobenzyl)-N-methyl-1-(1-piperazinyl)-1-indancarboxamide, its optical isomers, and also addition salts thereof with a pharmaceutically acceptable acid,
(1RS)-N-[3-fluoro-5-(trifluoromethyl)benzyl]-N-methyl-1-(1-piperazinyl)-1-indan-carboxamide, its optical isomers, and also addition salts thereof with a pharmaceutically acceptable acid,
(1RS)-1-[1-(3,5-difluorobenzyloxymethyl)indan-1-yl]piperazine, its optical isomers, and also addition salts thereof with a pharmaceutically acceptable acid,
N-(3-chloro-5-fluorobenzyl)-N-methyl-2-(1-piperazinyl)-2-indancarboxamide, and also addition salts thereof with a pharmaceutically acceptable acid,
1-[(1RS)-1-(3,5-difluorobenzyloxymethyl)indan-1-yl]piperazine, its optical isomers, and also addition salts thereof with a pharmaceutically acceptable acid,
(1RS)-N-(3,5-difluorobenzyl)-N-methyl-1-(1-piperazinyl)-1-indancarboxamide, its optical isomers, and also addition salts thereof with a pharmaceutically acceptable acid,
1-[(1RS)-1-(3,5-difluorobenzyloxymethyl)-5,6-difluoroindan-1-yl]piperazine, its optical isomers, and also addition salts thereof with a pharmaceutically acceptable acid, and 1-[(1RS)-1-(3-bromo-5-fluorobenzyloxymethyl)indan-1-yl]piperazine, its optical isomers, and also addition salts thereof with a pharmaceutically acceptable acid.

The invention relates also to a process for the preparation of compounds of formula (I), starting from the compound of formula (II):

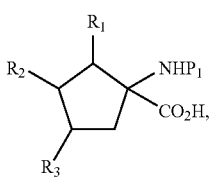
(II)

wherein $R_1$, $R_2$ and $R_3$ are as defined for formula (I) and $P_1$ represents a protecting group for the amine function, the acid function of which is protected to yield the compound of formula (III):

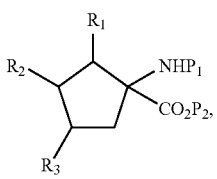
(III)

wherein $R_1$, $R_2$, $R_3$ and $P_1$ are as defined hereinbefore and $P_2$ represents a protecting group for the acid function which is different from $P_1$, the amine function of which is deprotected before reaction with the compound of formula (IV):

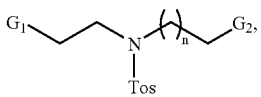
(IV)

wherein $G_1$ and $G_2$ each represent a halogen atom or a p-toluenesulphonyloxy group, Tos represents a para-toluenesulphonyl group, and n is as defined for formula (I), to yield the compound of formula (V)

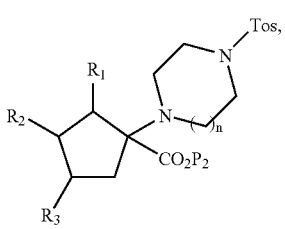
(V)

wherein $R_1$, $R_2$, $R_3$, $P_2$, n and Tos are as defined hereinbefore, from which the para-toluenesulphonyl group is cleaved, the acid function is deprotected and then the amine function is protected to yield the compound of formula (VI):

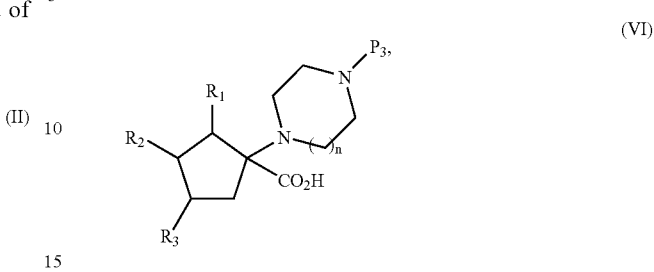
(VI)

wherein $R_1$, $R_2$, $R_3$ and n are as defined hereinbefore and $P_3$ represents a protecting group for the amine function, which compound of formula (VI) is reacted, when it is desired to obtain compounds of formula (I) wherein X represents —(CO)—NR$_4$-Ak- or —CH$_2$—NR$_4$-Ak, with a compound of formula (VII):

HNR$_4$-Ak-Ar          (VII), wherein $R_4$, Ak and Ar are as defined for formula (I), in the presence of one or more coupling agents, to yield, after deprotection of the ring amine function, compounds of formula (Ia), a particular case of the compounds of formula (I) wherein X represents a group —(CO)—NR$_4$-Ak:

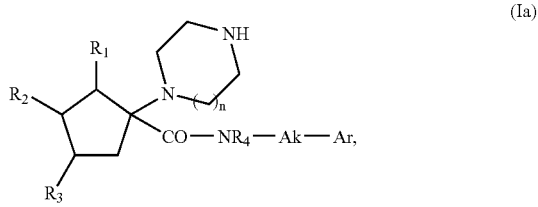
(Ia)

wherein $R_1$, $R_2$, $R_3$, n, $R_4$ and Ak are as defined hereinbefore and Ar is as defined for formula (I), which is reacted, when it is desired to obtain compounds of formula (Ib), a particular case of the compounds of formula (I) wherein X represents a group —CH$_2$—NR$_4$-Ak, with a reducing agent to yield compounds of formula (Ib):

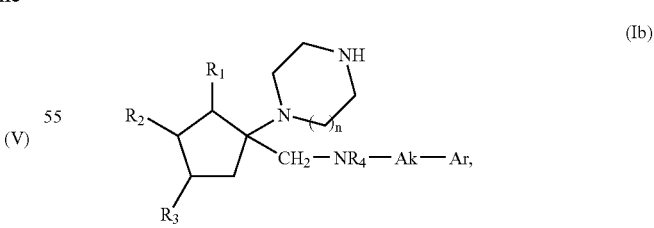
(Ib)

wherein $R_1$, $R_2$, $R_3$, n, $R_4$, Ak and Ar are as defined hereinbefore, or which compound of formula (VI) is esterified, when it is desired to obtain compounds of formula (I) wherein X represents a group —CH$_2$—OAk- or —CH$_2$—NR$_4$—(CO)—, to yield the compound of formula (VIII):

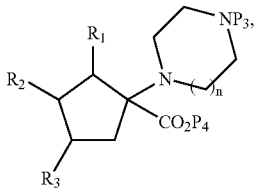
(VIII)

wherein $R_1$, $R_2$, $R_3$, n and $P_3$ are as defined hereinbefore and $P_4$ represents a benzyl or linear or branched $C_1$-$C_6$alkyl group, which is placed in the presence of a reducing agent to yield the alcohol of formula (IX):

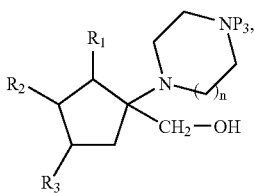
(IX)

wherein $R_1$, $R_2$, $R_3$, n and $P_3$ are as defined hereinbefore, which alcohol of formula (IX) is reacted, when it is desired to obtain compounds of formula (Ic), a particular case of the compounds of formula (I) wherein X represents the group —$CH_2$—O-Ak-, with a compound of formula (X):

Hal-Ak-Ar (X), wherein Ak and Ar are as defined for formula (I) and Hal represents a halogen atom, to yield, after deprotection of the ring amine function, compounds of formula (Ic):

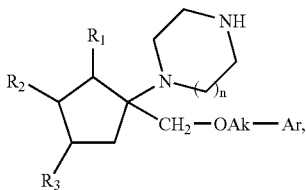
(Ic)

wherein $R_1$, $R_2$, $R_3$, n, Ak and Ar are as defined hereinbefore, or which alcohol of formula (IX) is converted by conventional reactions of organic chemistry into an amine of formula (XI):

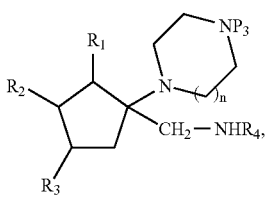
(XI)

wherein $R_1$, $R_2$, $R_3$, n, $R_4$ and $P_3$ are as defined hereinbefore, which is reacted with a compound of formula (XII):

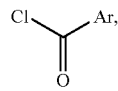
(XII)

wherein Ar is as defined for formula (I), to yield, after deprotection of the ring amine function, compounds of formula (Id), a particular case of the compounds of formula (I) wherein X represents a group —$CH_2$—$NR_4$—(CO)—:

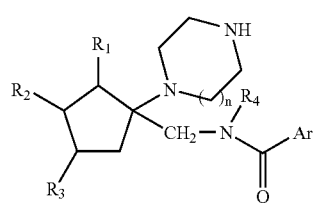
(Id)

wherein $R_1$, $R_2$, $R_3$, n, $R_4$ and Ar are as defined hereinbefore, which compounds of formulae (Ia), (Ib), (Ic) and (Id) are purified according to a conventional purification technique, are separated, when desired, into their optical isomers and are converted, when desired, into their addition salts with a pharmaceutically acceptable acid.

Compounds of formula (Ie), a particular case of the compounds of formula (I) wherein X represents the group of formula —$CH_2$O—$CH(CH_3)$—:

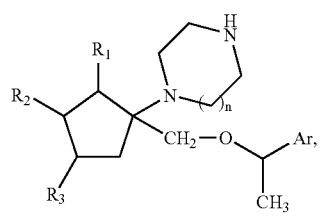
(Ie)

wherein $R_1$, $R_2$, $R_3$, n and Ar are as defined hereinbefore, can also be obtained by condensation of the compound of formula (IX) with the compound of formula (XIII):

Ar—$CO_2$H (XIII), wherein Ar is as defined hereinbefore, to yield the compound of formula (XIV):

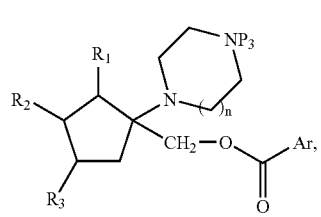
(XIV)

wherein $R_1$, $R_2$, $R_3$, n, Ar and $P_3$ are as defined hereinbefore, which is reacted with bis(cyclopentadienyl)dimethyltitanium to yield the compound of formula (XV):

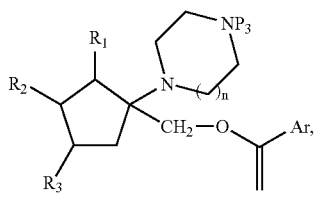

wherein $R_1$, $R_2$, $R_3$, n, Ar and $P_3$ are as defined hereinbefore, which is hydrogenated to yield the compound of formula (XVI):

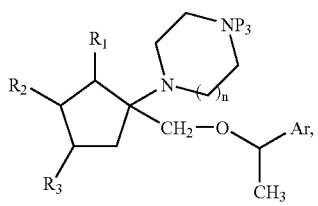

wherein $R_1$, $R_2$, $R_3$, n, Ar and $P_3$ are as defined hereinbefore, the amine function of which is deprotected to yield the compound of formula (Ie), which is separated, when desired, into its optical isomers and is converted, when desired, into its addition salts with a pharmaceutically acceptable acid.

The compounds of the present invention are serotonin reuptake inhibitors and $NK_1$ antagonists. They are useful as medicaments in the treatment of depressive states, anxiety states, impulsive disorders, aggressive behaviours, drug abuse, obesity and appetite disorders, pain and inflammation, dementias, psychotic states, disturbances of chronobiological rhythms, nausea and gastrointestinal disorders.

The present invention relates also to pharmaceutical compositions comprising, as active ingredient, a compound of formula (I), or an addition salt thereof with a pharmaceutically acceptable acid, in combination with one or more pharmaceutically acceptable, inert, non-toxic excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, gelatin capsules, capsules, suppositories, creams, ointments, dermal gels, injectable or drinkable preparations, aerosols, eye drops and nose drops.

The useful dosage varies according to the age and weight of the patient, the administration route, the nature and severity of the disorder, and the administration of any associated treatments and ranges from 0.5 to 500 mg per day in one or more administrations.

The Examples that follow illustrate the invention. The starting materials used are known products or are prepared according to known procedures. The various Preparations yield synthesis intermediates that are of use in preparation of the compounds of the invention.

The structures of the compounds described in the Examples were determined according to customary spectrophotometric techniques (infra-red, nuclear magnetic resonance, mass spectrometry).

A compound of configuration (1α) is understood to be a compound selected from the compounds of absolute configurations (1R) and (1S), it being understood that when the (1α) compound represents the compound of configuration (1R) the (1β) compound represents the other enantiomer.

A compound of configuration (1α') is understood to be a compound selected from the compounds of absolute configurations (1R) and (1S), it being understood that when the (1α') compound represents the compound configuration (1R) the (1β') represents the other enantiomer.

A compound of configuration (1RS) is understood to be a racemic mixture of the 2 enantiomers of absolute configurations (1R) and (1S).

Preparation 1: (1RS)-1-[4-(tert-butyloxycarbonyl)-1-piperazinyl]-1-indan-carboxylic acid Step A: Benzyl (1RS)-1-[(tert-butyloxycarbonyl)amino]-1-indancarboxylate.

To 0.140 mol of 1-[(tert-butyloxycarbonyl)amino]-1-indancarboxylic acid there are added 750 ml of dimethylformamide and then 0.147 mol of caesium carbonate. Stirring is then carried out for 2 hours 30 minutes at ambient temperature and there is then poured in, dropwise, over ½ hour, 0.145 mol of benzyl bromide dissolved in 150 ml of dimethylformamide, and stirring is carried out for 20 hours at ambient temperature.

The mineral salts are filtered off and the solvent is evaporated off. The residue is redissolved in ethyl acetate and washed with water. The organic phase is dried and then evaporated to yield the expected product.

IR v: 3284 nm-1—NH
1735-1672 $cm^{-1}$>C=0

Step B: Benzyl (1RS)-1-amino-1-indancarboxylate hydrochloride.

0.471 mol of the compound obtained in the step above are added to 2 liters of ethyl acetate. A stream of hydrogen chloride gas is passed through for 1 hour 15 minutes, with stirring, and then stirring is continued for 20 hours at ambient temperature. The expected product is obtained by evaporation of the ethyl acetate.

IR v: 1741 $cm^{-1}$>C=0

Step C: Benzyl (1RS)-1-[4-(para-toluenesulphonyl)-1-piperazinyl]-1-indancarboxylate.

To 0.235 mol of the compound obtained in the step above there are added 750 ml of dimethylformamide, 750 ml of diisopropylethylamine and 0.235 mol of N,N-bis(2-chloroethyl)para-toluenesulphonamide. Refluxing is carried out for 48 hours and then the solvents are evaporated off. The residue is dissolved in ethyl acetate and washed with water. The organic phase is dried and evaporated. The residue is purified by chromatography on silica gel, using a 98/2 methylene chloride/ethyl acetate mixture as eluant, to yield the expected product.

| IR | ν | C=O | 1728 cm$^{-1}$ |
|---|---|---|---|
|  |  | asymmetric SO$_2$ | 1348 cm$^{-1}$ |
|  |  | symmetric SO$_2$ | 1164 cm$^{-1}$ |

Step D: (1RS)-1-[4-(Para-toluenesulphonyl)-1-piperazinyl]-1-indancarboxylic acid.

To 0.181 mol of the compound obtained in the step above there are added 620 ml of dioxane, and then 620 ml of 1N sodium hydroxide solution and 360 ml of water. Refluxing is carried out for 20 hours and then the dioxane is evaporated off. Neutralisation is carried out by adding 620 ml of 1N hydrochloric acid, and then extraction with methylene chloride is carried out. The organic phase is dried and evaporated. The residue is crystallised from ethyl ether and then filtered off to yield the expected product.

| IR | ν | OH | 1800-3000 cm$^{-1}$ |
|---|---|---|---|
|  |  | C=O | 1706 cm$^{-1}$ |
|  |  | C=O | 1596 cm$^{-1}$ |
|  |  | SO$_2$ | 1348-1165 cm$^{-1}$ |
|  |  | CH... | 772-732 cm$^{-1}$ |

Step E: (1RS)-1-(1-piperazinyl)-1-indancarboxylic acid dihydrobromide.

To 100 ml of a 30% solution of hydrobromic acid in acetic acid there are added 40 ml of acetic acid, 12.5 mmol of naphthalene and 12.5 mmol of the compound obtained in the step above. Refluxing is carried out for 1 hour, followed by concentration. The residue is taken up in water, and the aqueous phase is washed with ethyl acetate and then evaporated. The solid residue is washed with acetonitrile and then dried to yield the expected product.
IR ν C=O 1740 cm$^{-1}$ Step F: (1RS)-1-[4-(tert-Butyloxycarbonyl)-1-piperazinyl]-1-indancarboxylic acid.

To 9.26 mmol of the compound obtained in the step above there are added 40 ml of dioxane and 37 ml of 1N sodium hydroxide solution. To the resulting solution there is added, dropwise and at ambient temperature, a solution of 10.2 mmol of di-tert-butyl dicarbonate in 100 ml of dioxane. Stirring is carried out for 5 hours and then the dioxane is evaporated off. The pH is brought to 4-5 using 1N hydrochloric acid, and saturation with sodium chloride and extraction with ethyl acetate are carried out. The organic phase is dried and evaporated to yield the expected product.

| IR | ν | OH | 2200-2300 cm$^{-1}$ |
|---|---|---|---|
|  |  | C=O | 1624-1731 cm$^{-1}$ |

PREPARATION 2: 2-[4-(tert-Butyloxycarbonyl)-1-piperazinyl]-2-indancarboxylic acid The expected product is obtained according to the procedure described in Preparation 1, replacing, in Step A, the 1-[(tert-butyloxycarbonyl)amino]-1-indancarboxylic acid by 2-[(tert-butyloxycarbonyl)amino]-2-indancarboxylic acid and the benzyl bromide by 1-bromoethane.

EXAMPLE 1

1-[(1RS)-1-(3,5Dibromobenzyloxymethyl)indan-1-yl]piperazine dihydrochloride

Step A: Benzyl (1RS)-1-[4-(tert-butyloxycarbonyl)-1-piperazinyl]-J-indancarboxylate.

To 63.5 mmol of the compound of Preparation 1 there are added 550 ml of dimethyl-formamide and 66 mmol of caesium carbonate; stirring is carried out for 2 hours at ambient temperature and there is then added, dropwise over ½ hour, a solution of 65.7 mmol of benzyl bromide in 50 ml of dimethylformamide. Stirring is continued for 20 hours at ambient temperature and the solvent is then evaporated off. The residue is taken up in ethyl acetate; the organic phase is washed with water, dried and evaporated to yield the expected product in the form of a colourless oil.

Step B (1RS)-1-[4-(tert-Butyloxycarbonyl)-1-piperazinyl]-1-hydroxymethylindan

To 250 ml of tetrahydrofuran and 63.2 mmol of lithium aluminium hydride there is added, over 1 hour 15 minutes, whilst maintaining the temperature of the reaction mixture below 20° C., a solution of 57.5 mmol of the compound obtained in the step above in 550 ml of tetrahydrofuran. After addition, stirring is continued for ½ hour at 20° C.; hydrolysis is then carried out with 50 ml of isopropanol, followed by 50 ml of saturated sodium chloride solution. Filtration is carried out and the filtrate is evaporated; the residue is redissolved in ethyl acetate and washed with water. The dried and evaporated organic phase yields the expected product.

| IR | ν | OH | 3440 cm$^{-1}$ |
|---|---|---|---|
|  |  | C=O | 1691 cm$^{-1}$ |

Step C: 4-(tert-Butyloxycarbonyl)-1-[(1RS)-1-(3,5-dibromobenzyloxymethyl)indan-1-yl]piperazine To 30 ml of dimethylformamide and 5.4 mmol of sodium hydride 95% there is added, over 10 minutes, a solution of 3.6 mmol of the compound obtained in the step above in 50 ml of dimethylformamide. Heating at 50-60° C. is carried out for ½ hour and the temperature is then allowed to return to ambient temperature. 0.36 mmol of tetrabutylammonium iodide is then added and then, over 10 minutes, a solution of 5.4 mmol of 3,5-dibromobenzyl bromide in 30 ml of dimethylformamide. Stirring is continued for 20 hours at ambient temperature.

The solvent is evaporated off, and the residue is then redissolved in ethyl acetate. Washing with water and with sodium chloride solution is carried out. The organic phase is dried and evaporated. The product is purified by chromatography on silica gel (eluant: CH$_2$Cl$_2$/AcOEt 90/10) to yield the expected product.
IR ν C=O 1688 cm$^{-1}$ Step D: 1-[(1RS)-1-(3,5-Dibromobenzyloxymethyl)
indan-1-yl]piperazine dihydrochloride To 2.75 mmol of the compound obtained in the step above dissolved in 30 ml of ethyl acetate there are added 15 ml of a 1N solution of hydrochloric acid in dioxane. After stirring for 20 hours at ambient temperature, the precipitate obtained is filtered off, washed with ethyl acetate and then redissolved in water. After evaporation and drying, the expected product is obtained.

Elemental Microanalysis:

|  | % C | % H | % N | % Cl |
|---|---|---|---|---|
| Calculated | 45.60 | 4.74 | 5.06 | 12.82 |
| Found | 45.95 | 4.80 | 5.12 | 13.16 |

EXAMPLE 2

1-[(1RS)-1-(3,5-Dimethylbenzyloxymethyl)indan-1-yl]piperazine dihydrochloride

The expected product is obtained according to the procedure described in Example 1, replacing the 3,5-dibromobenzyl bromide in Step C by 3,5-dimethylbenzyl bromide.

Elemental Microanalysis:

|  | % C | % H | % N | % Cl |
|---|---|---|---|---|
| Calculated | 65.24 | 7.62 | 6.62 | 16.75 |
| Found | 65.71 | 7.49 | 6.53 | 16.46 |

EXAMPLE 3

1-[2-(3,5-Dimethylbenzyloxymethyl)indan-2-yl]piperazine dihydrochloride

Step A: 2-[4-(tert-Butyloxycarbonyl)-1-piperazinyl]-2-hydroxymethylindan.

The expected product is obtained according to the procedure described in Steps A and B of Example 1, replacing the compound of Preparation 1 in Step A by the compound of Preparation 2.

Step B: 1-[2-(3,5-Dimethylbenzyloxymethyl)indan-2-yl]piperazine dihydrochloride.

The expected product is obtained according to the procedure described in Steps C and D of Example 1, starting from the compound obtained in Step A above and 3,5-dimethylbenzyl bromide.

Elemental Microanalysis:

|  | % C | % H | % N | % Cl |
|---|---|---|---|---|
| Calculated | 65.24 | 7.62 | 6.62 | 16.75 |
| Found | 65.92 | 7.52 | 6.64 | 16.91 |

EXAMPLE 4

(1RS)-N-(3,5-Dibromobenzyl)-1-(1-piperazinyl)-1-indancarboxamide dihydrochloride Step A: (1RS)-N-(3,5-Dibromobenzyl)-1-[4-(tert-butyloxycarbonyl)-1-piperazinyl]-1-1-indancarboxamide.

To 2 mmol of the compound of Preparation 1 there are added 50 ml of dimethylformamide, 2 mmol of 3,5-dibromobenzylamine, 2 mmol of 1-hydroxybenzotriazole and 2 mmol of dicyclohexylcarbodiimide. Stirring for 20 hours at ambient temperature and then evaporation are carried out. The residue is then taken up in ethyl acetate. The dicyclohexylurea formed is removed by filtration; the organic phase is then washed with saturated sodium bicarbonate solution, followed by saturated sodium chloride solution.

After drying, evaporation and purification by chromatography on silica gel (eluant: $CH_2Cl_2$/AcOEt 95/5), the expected product is obtained.

| IR | ν | NH | 3347 cm$^{-1}$ |
|---|---|---|---|
|  |  | C=O | 1668 cm$^{-1}$ |

Step B: (1RS)-N-(3,5-Dibromobenzyl)-1-(1-piperazinyl)-1-indancarboxamide dihydrochloride To 1.6 mmol of the compound obtained in the step above dissolved in 30 ml of ethyl acetate there are added 15 ml of a 4N solution of hydrochloric acid in dioxane, and the reaction mixture is then stirred for 20 hours at ambient temperature. The precipitate obtained is filtered off and then redissolved in 5 ml of water. After evaporating off the water and drying, the expected product is obtained.

Elemental Microanalysis:

|  | % C | % H | % N | % Cl |
|---|---|---|---|---|
| Calculated | 44.55 | 4.45 | 7.42 | 12.52 |
| Found | 44.92 | 4.61 | 7.44 | 11.54 |

EXAMPLE 5

N-[3,5-Bis(trifluoromethyl)benzyl]-2-(1-piperazinyl)-2-indan-carboxamide dihydrochloride The expected product is obtained according to the procedure of Example 4, starting from the compound of Preparation 2 and 3,5-bis(trifluoromethyl)benzylamine.

Elemental Microanalysis:

|  | % C | % H | % N | % Cl |
|---|---|---|---|---|
| Calculated | 51.44 | 4.63 | 7.72 | 11.88 |
| Found | 51.42 | 4.73 | 7.71 | 10.82 |

EXAMPLE 6

[3,5Bis(trifluoromethyl)phenyl]-N-{[2-(1-piperazinylindan-2-yl]-methyl}methanamine trihydrochloride To 3 mmol of the compound of Example 5 dissolved in 80 ml of tetrahydrofuran there are added, under nitrogen and over 20 minutes, 30 mmol of a 2N solution of borane dimethyl sulphide in tetrahydrofuran. The reaction mixture is then refluxed for 18 hours and subsequently returned to ambient temperature. 50 ml of 4N hydrochloric acid are then added dropwise and refluxing is subsequently carried out again for 20 hours, before evaporating off the solvents, making alkaline with sodium hydroxide solution and extracting the reaction mixture with ethyl acetate. The organic phase is washed with saturated sodium chloride solution, dried and then evaporated. After purification by chromatography, conversion into a salt using hydrochloric acid and evaporation, the expected product is obtained after drying.

Elemental Microanalysis:

|  | % C | % H | % N | % Cl |
|---|---|---|---|---|
| Calculated | 49.69 | 5.02 | 7.56 | 17.22 |
| Found | 49.77 | 5.01 | 7.38 | 17.37 |

EXAMPLE 7

N-Benzyl-N-methyl-2-(1-piperazinyl)-2-indancarboxamide dihydrochloride

The expected product is obtained according to the procedure of Example 4, starting from the compound of Preparation 2 and N-benzyl-N-methylamine.

Elemental Microanalysis:

|  | % C | % H | % N | % Cl |
|---|---|---|---|---|
| Calculated | 63.66 | 6.99 | 9.95 | 15.37 |
| Found | 63.64 | 6.71 | 10.24 | 15.86 |

EXAMPLE 8

1-[(1α)-1-(3,5-Dimethylbenzyloxymethyl)indan-1-yl]piperazine dihydrochloride

The expected product is obtained by separation of the compound of Example 2 on a chiral HPLC column.

EXAMPLE 9

1-[(1β)-1-(3,5-Dimethylbenzyloxymethyl)indan-1-yl]piperazine dihydrochloride

The expected product is the second of the enantiomers obtained by separation of the compound of Example 2 on a chiral HPLC column.

EXAMPLE 10

(1RS)-N-[3,5-Bis(trifluoromethyl)benzyl]-1-(1-piperazinyl)-1-indan-carboxamide dihydrochloride The expected product is obtained according to the procedure of Example 4, replacing the 3,5-dibromobenzylamine in Step A by 3,5-bis(trifluoromethyl)benzylamine.

Elemental Microanalsis:

|  | % C | % H | % N | % Cl |
|---|---|---|---|---|
| Calculated | 50.75 | 4.63 | 7.72 | 13.03 |
| Found | 51.08 | 4.86 | 7.79 | 13.45 |

EXAMPLE 11

(1RS)-N-Benzyl-N-methyl-1-(1-piperazinyl)-1-indancarboxamide dihydrochloride

The expected product is obtained according to the procedure of Example 4, starting from the compound of Preparation 1 and N-methylbenzylamine.

Elemental Microanalysis:

|  | % C | % H | % N | % Cl |
|---|---|---|---|---|
| Calculated | 62.56 | 6.92 | 9.95 | 16.79 |
| Found | 62.27 | 6.86 | 9.73 | 17.91 |

EXAMPLE 12

1-[2-(Biphenyl-4-ylmethoxymethyl)indan-2-yl]piperazine dihydrochloride

The expected product is obtained according to the procedure of Example 1, starting from the compound of Preparation 2 and biphenyl-4-ylmethyl bromide.

Elemental Microanalysis:

|  | % C | % H | % N | % Cl |
|---|---|---|---|---|
| Calculated | 68.78 | 6.84 | 5.94 | 15.04 |
| Found | 69.38 | 7.09 | 5.99 | 15.03 |

EXAMPLE 13

1-[2-(3,5-Dimethoxybenzyloxymethyl)indan-2-yl]piperazine dihydrochloride

The expected product is obtained according to the procedure of Example 1, starting from the compound of Preparation 2 and 3,5-dimethoxybenzyl bromide.

Elemental Microanalysis:

|  | % C | % H | % N | % Cl |
|---|---|---|---|---|
| Calculated | 60.66 | 7.08 | 6.15 | 15.57 |
| Found | 60.96 | 7.30 | 6.07 | 15.71 |

EXAMPLE 14

1-[2-(3,5-Dichlorobenzyloxymethyl)indan-2-yl]piperazine dihydrochloride

The expected product is obtained according to the procedure of Example 1, starting from the compound of Preparation 2 and 3,5-dichlorobenzyl bromide.

Elemental Microanalysis:

|  | % C | % H | % N | % Cl |
|---|---|---|---|---|
| Calculated | 54.33 | 5.64 | 6.03 | 30.55 |
| Found | 54.08 | 5.31 | 6.12 | 30.15 |

EXAMPLE 15

1-[2-3,4-Dichlorobenzyloxymethyl)indan-2-yl]piperazine dihydrochloride

The expected product is obtained according to the procedure of Example 1, starting from the compound of Preparation 2 and 3,4-dichlorobenzyl bromide.

Elemental Microanalysis:

|  | % C | % H | % N | % Cl |
|---|---|---|---|---|
| Calculated | 54.33 | 5.64 | 6.03 | 30.55 |
| Found | 53.99 | 5.46 | 6.03 | 29.99 |

EXAMPLE 16

1-[2-(3,5-Dibromobenzyloxymethyl)indan-2-yl]piperazine dihydrochloride

The expected product is obtained according to the procedure of Example 1, starting from the compound of Preparation 2 and 3,5-dibromobenzyl bromide.

Elemental Microanalysis:

|  | % C | % H | % N | % Cl |
|---|---|---|---|---|
| Calculated | 45.60 | 4.74 | 5.06 | 12.82 |
| Found | 45.48 | 4.83 | 5.03 | 12.79 |

EXAMPLE 17

1-[2-[3,5-Bis(trifluoromethyl)benzyloxymethyl]indan-2-yl]-piperazine dihydrochloride The expected product is obtained according to the procedure of Example 1, starting from the compound of Preparation 2 and 3,5-bis(trifluoromethyl)benzyl bromide.

Elemental Microanalysis:

|  | % C | % H | % N | % Cl |
|---|---|---|---|---|
| Calculated | 51.99 | 4.93 | 5.27 | 13.34 |
| Found | 52.48 | 5.05 | 5.34 | 13.12 |

EXAMPLE 18

(1RS-N-Benzyl-1-(1-piperazinyl)-1-indancarboxamide dihydrochloride

The expected product is obtained according to the procedure of Example 4, replacing the 3,5-dibromobenzylamine in Step A by benzylamine.

Elemental Microanalysis:

|  | % C | % H | % N | % Cl |
|---|---|---|---|---|
| Calculated | 61.77 | 6.66 | 10.29 | 17.36 |
| Found | 61.63 | 7.06 | 10.24 | 17.38 |

EXAMPLE 19

1-[2-(Naphth-2-ylmethoxymethyl)indan-2-yl]piperazine dihydrochloride

The expected product is obtained according to the procedure of Example 1, starting from the compound of Preparation 2 and naphth-2-ylmethyl bromide.

Elemental Microanalysis:

|  | % C | % H | % N | % Cl |
|---|---|---|---|---|
| Calculated | 67.41 | 6.79 | 6.29 | 15.92 |
| Found | 66.99 | 7.18 | 6.29 | 15.69 |

EXAMPLE 20

(1RS)-N-[3,5-Bis(trifluoromethyl)benzyl]-N-methyl-1-(1-piperazinyl)-1-indancarboxamide dihydrochloride The expected product is obtained according to the procedure of Example 4, starting from the compound of Preparation 1 and N-methyl-3,5-bis(trifluoromethyl)benzylamine.

Elemental Microanalysis:

|  | % C | % H | % N | % Cl |
|---|---|---|---|---|
| Calculated | 51.62 | 4.87 | 7.53 | 12.70 |
| Found | 51.40 | 4.85 | 7.48 | 11.77 |

EXAMPLE 21

N-(3,5Dichlorobenzyl)₂-(1-piperazinyl)-2-indancarboxamide dihydrochloride

The expected product is obtained according to the procedure of Example 4, starting from the compound of Preparation 2 and 3,5-dichlorobenzylamine.

Elemental Microanalysis:

|  | % C | % H | % N | % Cl |
|---|---|---|---|---|
| Calculated | 52.85 | 5.28 | 8.80 | 29.71 |
| Found | 53.30 | 5.34 | 9.00 | 28.89 |

EXAMPLE 22

(1α)-N-[(1S)-1-Phenethyl]-1-(1-piperazinyl)-1-indancarboxamide dihydrochloride

Step A: (1RS)-N-[(1S)-1-Phenethyl]-1-[4-(tert-butyloxycarbonyl)-1-piperazinyl-1-indancarboxamide The expected product is obtained according to the procedure described in Step A of Example 4, starting from the compound of Preparation 1 and (1S)-1-phenethylamine.

Step B: (1α)-N-[(1S)-1-Phenethyl]-1-[4-(tert-butyloxycarbonyl)-1-piperazinyl-1-indancarboxamide The expected product is obtained by separation, by means of chromatography on silica, of the diastereoisomeric mixture obtained in Step A.

Step C: (1α)-N-[(1S)-1-Phenethyl]-1-(1-piperazinyl)-1-indancarboxamide dihydrochloride Starting from the compound obtained in Step B, the expected product is obtained according to the procedure described in Step B of Example 4.

Elemental Microanalysis:

|  | % C | % H | % N | % Cl |
|---|---|---|---|---|
| Calculated | 62.56 | 6.92 | 9.95 | 16.79 |
| Found | 62.69 | 7.21 | 9.85 | 16.54 |

EXAMPLE 23

(1β)-N-[(1S)-1-Phenethyl]-1-(1-piperazinyl)-1-indancarboxamide dihydrochloride

The expected product is obtained according to the procedure described in Step B of Example 4, starting from the second of the diastereoisomers separated in Step B of Example 22.

Elemental Microanalysis:

|  | % C | % H | % N | % Cl |
|---|---|---|---|---|
| Calculated | 62.56 | 6.92 | 9.95 | 16.79 |
| Found | 62.57 | 7.08 | 9.90 | 16.32 |

EXAMPLE 24

(1α)-N-[(1R)-1-Phenethyl]-1-(1-piperazinyl)-1-indancarboxamide dihydrochloride

Step A: (1RS)-N-[(1R)-1-Phenethyl]-1-[4-(tert-butyloxycarbonyl)-1-piperazinyl]-1-indancarboxamide.

The expected product is obtained according to the procedure described in Step A of Example 4, starting from the compound of Preparation 1 and (1R)-1-phenethylamine.

Step B: (1α)-N-[(1R)-1-Phenethyl]-1-[4-(tert-butyloxycarbonyl)-1-piperazinyl]-1-indancarboxamide The expected product is obtained by separation, by means of chromatography on silica, of the diastereoisomeric mixture obtained in Step A.

Step C: (1α)-N-[(1R)-1-Phenethyl]-1-(1-piperazinyl)-1-indancarboxamide dihydrochloride The expected product is obtained according to the procedure described in Step B of Example 4, starting from the compound obtained in Step B.

Elemental Microanalysis:

|  | % C | % H | % N | % Cl |
|---|---|---|---|---|
| Calculated | 62.56 | 6.92 | 9.95 | 16.79 |
| Found | 62.69 | 7.21 | 9.85 | 16.54 |

EXAMPLE 25

(1β)-N-[(1R)-1-Phenethyl]-1-(1-piperazinyl)-1-indancarboxamide dihydrochloride

The expected product is obtained according to the procedure described in Step B of Example 4, starting from the second of the diastereoisomers separated in Step B of Example 24.

Elemental Microanalysis:

|  | % C | % H | % N | % Cl |
|---|---|---|---|---|
| Calculated | 62.56 | 6.92 | 9.95 | 16.79 |
| Found | 62.71 | 7.25 | 9.92 | 16.27 |

EXAMPLE 26

(1RS)-N-(2-Phenethyl)-1-(1-piperazinyl)-1-indan-carboxamide dihydrochloride

The expected product is obtained according to the procedure of Example 4, replacing the 3,5-dibromobenzylamine in Step A by 2-phenethylamine.

Elemental Microanalysis:

|  | % C | % H | % N | % Cl |
|---|---|---|---|---|
| Calculated | 62.56 | 6.92 | 9.95 | 16.79 |
| Found | 62.34 | 7.17 | 9.83 | 16.65 |

EXAMPLE 27

(1RS)-N-(3,4-Dichlorobenzyl)-1-(1-piperazinyl)-1-indancarboxamide dihydrochloride The expected product is obtained according to the procedure of Example 4, replacing the 3,5-dibromobenzylamine in Step A by 3,4-dichlorobenzylamine.

Elemental Microanalysis:

|  | % C | % H | % N | % Cl |
|---|---|---|---|---|
| Calculated | 52.85 | 5.28 | 8.80 | 29.71 |
| Found | 53.26 | 5.52 | 8.83 | 28.98 |

EXAMPLE 28

2-(1-piperazinyl)N-(3-pyridylmethyl)-2-indancarboxamide trihydrochloride

The expected product is obtained according to the procedure of Example 4, starting from the compound of Preparation 2 and 3-pyridylmethylamine.

Elemental Microanalysis:

|  | % C | % H | % N | % Cl |
|---|---|---|---|---|
| Calculated | 53.88 | 6.10 | 12.57 | 23.86 |
| Found | 53.94 | 6.20 | 12.30 | 23.76 |

EXAMPLE 29

2-(1-piperazinyl)N-(2-thienylmethyl)-2-indancarboxamide dihydrochloride

The expected product is obtained according to the procedure of Example 4, starting from the compound of Preparation 2 and 2-thienylmethylamine.

Elemental Microanalysis:

|  | % C | % H | % N | % S | % Cl |
|---|---|---|---|---|---|
| Calculated | 55.07 | 6.08 | 10.14 | 7.74 | 17.11 |
| Found | 54.96 | 6.07 | 10.75 | 7.53 | 16.56 |

EXAMPLE 30

2-(1-piperazinyl)-N-[4-(trifluoromethyl)benzyl]-2-indan-carboxamide dihydrochloride The expected product is obtained according to the procedure of Example 4, starting from the compound of Preparation 2 and 4-(trifluoromethyl)benzylamine.

Elemental Microanalysis:

|  | % C | % H | % N | % Cl |
|---|---|---|---|---|
| Calculated | 55.47 | 5.50 | 8.82 | 14.88 |
| Found | 55.13 | 5.43 | 8.93 | 14.98 |

EXAMPLE 31

N-(2-Phenethyl)-2-(1-piperazinyl)-2-indancarboxamide dihydrochloride

The expected product is obtained according to the procedure of Example 4, starting from the compound of Preparation 2 and 2-phenethylamine.

Elemental Microanalysis:

|  | % C | % H | % N | % Cl |
|---|---|---|---|---|
| Calculated | 62.56 | 6.92 | 9.95 | 16.79 |
| Found | 63.42 | 6.91 | 10.06 | 16.63 |

EXAMPLE 32

N-(1-Naphthylmethyl)-2-(1-piperazinyl)-2-indancarboxamide dihydrochloride

The expected product is obtained according to the procedure of Example 4, starting from the compound of Preparation 2 and 1-naphthylmethylamine.

Elemental Microanalysis:

|  | % C | % H | % N | % Cl |
|---|---|---|---|---|
| Calculated | 65.50 | 6.38 | 9.17 | 15.47 |
| Found | 65.86 | 6.52 | 9.83 | 14.72 |

EXAMPLE 33

(1RS)-N-(2,4-Dichlorobenzyl)-1-(1-piperazinyl)-1-indancarboxamide dihydrochloride The expected product is obtained according to the procedure of Example 4, replacing the 3,5-dibromobenzylamine in Step A by 2,4-dichlorobenzylamine.

Elemental Microanalysis:

|  | % C | % H | % N | % Cl |
|---|---|---|---|---|
| Calculated | 52.85 | 5.28 | 8.80 | 29.71 |
| Found | 53.69 | 5.31 | 8.84 | 30.27 |

EXAMPLE 34

(1RS)-1-(1-piperazinyl)-N-(3-thienylmethyl)-1-indancarboxamide dihydrochloride

The expected product is obtained according to the procedure of Example 4, replacing the 3,5-dibromobenzylamine in Step A by 3-thienylmethylamine.

Elemental Microanalysis:

|  | % C | % H | % N | % S | % Cl |
|---|---|---|---|---|---|
| Calculated | 55.07 | 6.08 | 10.14 | 7.74 | 17.11 |
| Found | 55.68 | 6.33 | 10.28 | 7.62 | 17.79 |

EXAMPLE 35

(1RS)-1-(1-piperazinyl)-N-(2-thienylmethyl)-1-indancarboxamide dihydrochloride

The expected product is obtained according to the procedure of Example 4, replacing the 3,5-dibromobenzylamine in Step A by 2-thienylmethylamine.

Elemental Microanalysis:

|  | % C | % H | % N | % S | % Cl |
|---|---|---|---|---|---|
| Calculated | 55.07 | 6.08 | 10.14 | 7.74 | 17.11 |
| Found | 55.73 | 6.35 | 10.30 | 7.76 | 17.49 |

EXAMPLE 36

(1RS)-N-(3,5-Dichlorobenzyl)-1-(1-piperazinyl)-1-indancarboxamide dihydrochloride The expected product is obtained according to the procedure of Example 4, replacing the 3,5-dibromobenzylamine in Step A by 3,5-dichlorobenzylamine.

Elemental Microanalysis:

|  | % C | % H | % N | % Cl |
|---|---|---|---|---|
| Calculated | 66.94 | 6.45 | 8.67 | 14.64 |
| Found | 66.26 | 6.41 | 8.57 | 14.09 |

EXAMPLE 37

N-(Biphenyl-4-ylmethyl)-2-(1-piperazinyl)-2-indancarboxamide dihydrochloride

The expected product is obtained according to the procedure of Example 4, starting from the compound of Preparation 2 and biphenyl-4-ylmethylamine.

Elemental Microanalysis:

|  | % C | % H | % N | % Cl |
|---|---|---|---|---|
| Calculated | 66.94 | 6.45 | 8.67 | 14.64 |
| Found | 66.26 | 6.41 | 8.57 | 14.09 |

EXAMPLE 38

N-(3,5Dimethylbenzyl)-2-(1-piperazinyl)-2-indancarboxamide dihydrochloride

The expected product is obtained according to the procedure of Example 4, starting from the compound of Preparation 2 and 3,5-dimethylbenzylamine.

Elemental Microanalysis:

|  | % C | % H | % N | % Cl |
|---|---|---|---|---|
| Calculated | 63.30 | 7.16 | 9.63 | 16.25 |
| Found | 63.50 | 7.28 | 10.23 | 16.19 |

EXAMPLE 39

N-[(1R)-1-Phenethyl]-2-(1-piperazinyl)-2-indancarboxamide dihydrochloride

The expected product is obtained according to the procedure of Example 4, starting from the compound of Preparation 2 and (1R)-1-phenethylamine.

Elemental Microanalysis:

|  | % C | % H | % N | % Cl |
|---|---|---|---|---|
| Calculated | 62.56 | 6.92 | 9.95 | 16.79 |
| Found | 62.49 | 7.03 | 10.44 | 16.97 |

EXAMPLE 40

N-[(1S)-1-Phenethyl]-2-(1-piperazinyl)-2-indancarboxamide dihydrochloride

The expected product is obtained according to the procedure of Example 4, starting from the compound of Preparation 2 and (1S)-1-phenethylamine.

Elemental Microanalysis:

|  | % C | % H | % N | % Cl |
|---|---|---|---|---|
| Calculated | 62.56 | 6.92 | 9.95 | 16.79 |
| Found | 62.83 | 7.10 | 10.34 | 16.19 |

EXAMPLE 41

(1RS)-N-(2-Methoxybenzyl)-1-(1-piperazinyl)-1-indancarboxamide dihydrochloride The expected product is obtained according to the procedure of Example 4, starting from the compound of Preparation 1 and 2-methoxybenzylamine.

Elemental Microanalysis:

|  | % C | % H | % N | % Cl |
|---|---|---|---|---|
| Calculated | 60.27 | 6.67 | 9.58 | 16.17 |
| Found | 59.71 | 6.91 | 9.41 | 15.88 |

EXAMPLE 42

(1RS)-N-(3,5-Dimethylbenzyl)-1-(1-piperazinyl)-1-indancarboxamide dihydrochloride The expected product is obtained according to the procedure of Example 4, starting from the compound of Preparation 1 and 3,5-dimethylbenzylamine.

Elemental Microanalysis:

|  | % C | % H | % N | % Cl |
|---|---|---|---|---|
| Calculated | 63.30 | 7.16 | 9.63 | 16.25 |
| Found | 62.89 | 7.53 | 9.44 | 16.06 |

EXAMPLE 43

2-(1-piperazinyl)N-(3-thienylmethyl)-2-indancarboxamide dihydrochloride

The expected product is obtained according to the procedure of Example 4, starting from the compound of Preparation 2 and 3-thienylmethylamine.

Elemental Microanalysis:

|  | % C | % H | % N | % S | % Cl |
|---|---|---|---|---|---|
| Calculated | 55.07 | 6.08 | 10.14 | 7.74 | 17.11 |
| Found | 55.34 | 6.53 | 9.93 | 7.96 | 17.70 |

EXAMPLE 44

N-(3,5Difluorobenzyl)-2-(1-piperazinyl)-2-indancarboxamide dihydrochloride

The expected product is obtained according to the procedure of Example 4, starting from the compound of Preparation 2 and 3,5-difluorobenzylamine.

Elemental Microanalysis:

|  | % C | % H | % N | % Cl |
|---|---|---|---|---|
| Calculated | 56.76 | 5.67 | 9.46 | 15.96 |
| Found | 57.26 | 5.74 | 9.45 | 15.41 |

EXAMPLE 45

N-(4-Methoxybenzyl)-2-1-piperazinyl)-2-indancarboxamide dihydrochloride

The expected product is obtained according to the procedure of Example 4, starting from the compound of Preparation 2 and 4-methoxybenzylamine.

Elemental Microanalysis:

|  | % C | % H | % N | % Cl |
|---|---|---|---|---|
| Calculated | 60.27 | 6.67 | 9.58 | 16.17 |
| Found | 59.45 | 6.79 | 10.41 | 16.36 |

EXAMPLE 46

N-(4-Bromobenzyl)-2-(1-piperazinyl)-2-indancarboxamide dihydrochloride

The expected product is obtained according to the procedure of Example 4, starting from the compound of Preparation 2 and 4-bromobenzylamine.

Elemental Microanalysis

|  | % C | % H | % N | % Cl |
|---|---|---|---|---|
| Calculated | 51.76 | 5.38 | 8.62 | 14.55 |
| Found | 52.30 | 5.36 | 8.90 | 13.95 |

EXAMPLE 47

N-(3-Bromobenzyl)-2-(1-piperazinyl)-2-indancarboxamide dihydro chloride

The expected product is obtained according to the procedure of Example 4, starting from the compound of Preparation 2 and 3-bromobenzylamine.

Elemental Microanalysis:

|  | % C | % H | % N | % Cl |
|---|---|---|---|---|
| Calculated | 51.76 | 5.38 | 8.62 | 14.55 |
| Found | 52.08 | 5.60 | 8.84 | 14.43 |

EXAMPLE 48

N-4-Chlorobenzyl)-2-(1-piperazinyl)-2-indancarboxamide dihydrochloride

The expected product is obtained according to the procedure of Example 4, starting from the compound of Preparation 2 and 4-chlorobenzylamine.

Elemental Microanalysis:

|  | % C | % H | % N | % Cl |
|---|---|---|---|---|
| Calculated | 56.96 | 5.92 | 9.49 | 24.02 |
| Found | 57.22 | 6.03 | 9.46 | 24.07 |

EXAMPLE 49

N-Benzyl-2-(1-piperazinyl)-2-indancarboxamide dihydrochloride

The expected product is obtained according to the procedure of Example 4, starting from the compound of Preparation 2 and benzylamine.

Elemental Microanalysis:

|  | % C | % H | % N | % Cl |
|---|---|---|---|---|
| Calculated | 61.77 | 6.66 | 10.29 | 17.36 |
| Found | 61.09 | 6.74 | 10.24 | 16.80 |

EXAMPLE 50

(1RS)-N-(3,5-Dibromobenzyl)-N-methyl-1-(1-piperazinyl)-1-indan-carboxamide dihydrochloride The expected product is obtained according to the procedure of Example 4, starting from the compound of Preparation 1 and N-methyl-3,5-dibromobenzylamine.

Elemental Microanalysis:

|  | % C | % H | % N | % Cl |
|---|---|---|---|---|
| Calculated | 45.54 | 4.69 | 7.24 | 12.22 |
| Found | 45.11 | 4.73 | 7.14 | 12.96 |

EXAMPLE 51

(1RS)-1-[1-(3,5-Bis(trifluoromethyl)benzyloxymethyl)indan-1-yl]-piperazine dihydrochloride The expected product is obtained according to the procedure of Example 1, starting from the compound of Preparation 1 and 3,5-bis(trifluoromethyl)benzyl bromide.

Elemental Microanalysis:

|  | % C | % H | % N | % Cl |
|---|---|---|---|---|
| Calculated | 51.99 | 4.93 | 5.27 | 13.34 |
| Found | 52.31 | 4.77 | 5.28 | 13.54 |

EXAMPLE 52

1-[(1RS)-1-(3,5-Dichlorobenzyloxymethyl)indan-1-yl]piperazine dihydrochloride The expected product is obtained according to the procedure of Example 1, starting from the compound of Preparation 1 and 3,5-dichlorobenzyl bromide.

Elemental Microanalysis:

|  | % C | % H | % N | % Cl |
|---|---|---|---|---|
| Calculated | 54.33 | 5.64 | 6.03 | 30.55 |
| Found | 54.97 | 5.81 | 6.00 | 29.88 |

EXAMPLE 53

1-[(1RS)-1-(3-(Trifluoromethyl)benzyloxymethyl)indan-1-yl]-piperazine dihydrochloride The expected product is obtained according to the procedure of Example 1, starting from the compound of Preparation 1 and 3-(trifluoromethyl)benzyl bromide.

Elemental Microanalysis:

|  | % C | % H | % N | % Cl |
|---|---|---|---|---|
| Calculated | 57.03 | 5.87 | 6.05 | 15.30 |
| Found | 56.75 | 6.33 | 5.81 | 15.16 |

EXAMPLE 54

2-(1-piperazinyl)-N-(2-pyridylmethyl)-2-indancarboxamide trihydrochloride

The expected product is obtained according to the procedure of Example 4, starting from the compound of Preparation 2 and 2-pyridylmethylamine.

Elemental Microanalysis:

|            | % C   | % H  | % N   | % Cl  |
|------------|-------|------|-------|-------|
| Calculated | 53.88 | 6.10 | 12.57 | 23.86 |
| Found      | 52.54 | 6.13 | 12.00 | 23.85 |

EXAMPLE 55

2-(1-piperazinyl)-N-(3-pyridylmethyl)-2-indancarboxamide trihydrochloride

The expected product is obtained according to the procedure of Example 4, starting from the compound of Preparation 2 and 3-pyridylmethylamine.

Elemental Microanalysis:

|            | % C   | % H  | % N   | % Cl  |
|------------|-------|------|-------|-------|
| Calculated | 53.88 | 6.10 | 12.57 | 23.86 |
| Found      | 53.92 | 5.94 | 12.43 | 24.62 |

EXAMPLE 56

N-(2-Bromobenzyl)-2-(1-piperazinyl)-2-indancarboxamide dihydrochloride

The expected product is obtained according to the procedure of Example 4, starting from the compound of Preparation 2 and 2-bromobenzylamine.

Elemental Microanalysis:

|            | % C   | % H  | % N  | % Cl  |
|------------|-------|------|------|-------|
| Calculated | 51.76 | 5.38 | 8.62 | 14.55 |
| Found      | 52.54 | 5.33 | 8.66 | 13.77 |

EXAMPLE 57

N-(4-Fluorobenzyl)-2-(1-piperazinyl)-2-indancarboxamide dihydrochloride

The expected product is obtained according to the procedure of Example 4, starting from the compound of Preparation 2 and 4-fluorobenzylamine.

Elemental Microanalysis:

|            | % C   | % H  | % N  | % Cl  |
|------------|-------|------|------|-------|
| Calculated | 59.16 | 6.15 | 9.86 | 16.63 |
| Found      | 58.93 | 6.04 | 9.69 | 16.81 |

EXAMPLE 58

N-(4-Methylbenzyl)-2-(1-piperazinyl)-2-indancarboxamide dihydrochloride

The expected product is obtained according to the procedure of Example 4, starting from the compound of Preparation 2 and 4-methylbenzylamine.

Elemental Microanalysis:

|            | % C   | % H  | % N  | % Cl  |
|------------|-------|------|------|-------|
| Calculated | 62.56 | 6.92 | 9.95 | 16.79 |
| Found      | 62.15 | 6.60 | 9.78 | 17.06 |

EXAMPLE 59

N-(3,5-Dibromobenzyl)-2-(1-piperazinyl)-2-indancarboxamide dihydrochloride

The expected product is obtained according to the procedure of-Example 4, starting from the compound of Preparation 2 and 3,5-dibromobenzylamine.

Elemental Microanalysis:

|            | % C   | % H  | % N  | % Cl  |
|------------|-------|------|------|-------|
| Calculated | 44.55 | 4.45 | 7.42 | 12.52 |
| Found      | 44.53 | 4.76 | 7.35 | 12.22 |

EXAMPLE 60

N-[3,5 Bis(trifluoromethyl)benzyl]-N-methyl-2-(1-piperazinyl)-2-indancarboxamide dihydrochloride The expected product is obtained according to the procedure of Example 4, starting from the compound of Preparation 2 and N-methyl-3,5-bis(trifluoromethyl)benzylamine.

Elemental Microanalysis:

|            | % C   | % H  | % N  | % Cl |
|------------|-------|------|------|------|
| Calculated | 53.37 | 4.94 | 7.78 | 9.84 |
| Found      | 53.21 | 5.15 | 7.63 | 9.78 |

EXAMPLE 61

2-(1-piperazinyl)-N-[4-(trifluoromethyl)benzyl]-2-indan-carboxamide dihydrochloride The expected product is obtained according to the procedure of Example 4, starting from the compound of Preparation 2 and 4-(trifluoromethyl)benzylamine.

Elemental Microanalysis:

|  | % C | % H | % N | % Cl |
| --- | --- | --- | --- | --- |
| Calculated | 55.47 | 5.50 | 8.82 | 14.88 |
| Found | 55.24 | 5.32 | 8.62 | 14.70 |

EXAMPLE 62

N-(2-Naphthylmethyl)-2-(1-piperazinyl)-2-indancarboxamide dihydrochloride

The expected product is obtained according to the procedure of Example 4, starting from the compound of Preparation 2 and 2-naphthylmethylamine.

Elemental Microanalysis:

|  | % C | % H | % N | % Cl |
| --- | --- | --- | --- | --- |
| Calculated | 65.50 | 6.38 | 9.17 | 15.47 |
| Found | 66.04 | 6.22 | 9.00 | 15.29 |

EXAMPLE 63

N-(3,5Difluorobenzyl)-2-(1-piperazinyl)-2-indancarboxamide dihydrochloride

The expected product is obtained according to the procedure of Example 4, starting from the compound of Preparation 2 and 3,5-difluorobenzylamine.

Elemental Microanalysis:

|  | % C | % H | % N | % Cl |
| --- | --- | --- | --- | --- |
| Calculated | 56.76 | 5.67 | 9.46 | 15.96 |
| Found | 56.87 | 5.81 | 9.49 | 15.99 |

EXAMPLE 64

(1RS)-1-[1-(3-Fluoro-5-(trifluoromethyl)benzyloxymethyl)indan-1-yl]piperazine dihydrochloride The expected product is obtained according to the procedure of Example 1, starting from the compound of Preparation 1 and 3-fluoro-5-(trifluoromethyl)benzyl bromide.

Elemental Microanalysis:

|  | % C | % H | % N | % Cl |
| --- | --- | --- | --- | --- |
| Calculated | 54.89 | 5.44 | 5.82 | 14.73 |
| Found | 54.78 | 5.58 | 5.79 | 14.65 |

EXAMPLE 65

(1RS)-1-(1-piperazinyl)-N-[3-(trifluoromethyl)benzyl]-1-indan-carboxamide dihydrochloride The expected product is obtained according to the procedure of Example 4, starting from the compound of Preparation 1 and 3-(trifluoromethyl)benzylamine.

Elemental Microanalysis:

|  | % C | % H | % N | % Cl |
| --- | --- | --- | --- | --- |
| Calculated | 55.47 | 5.50 | 8.82 | 14.88 |
| Found | 56.07 | 5.78 | 8.79 | 14.73 |

EXAMPLE 66

(1RS)-1-(1-piperazinyl)-N-methyl-N-[3-(trifluoromethyl)benzyl]-1-indancarboxamide dihydrochloride The expected product is obtained according to the procedure of Example 4, starting from the compound of Preparation 1 and N-methyl-3-(trifluoromethyl)benzylamine.

Elemental Microanalysis:

|  | % C | % H | % N | % Cl |
| --- | --- | --- | --- | --- |
| Calculated | 56.33 | 5.76 | 8.57 | 14.46 |
| Found | 56.10 | 5.78 | 8.47 | 14.72 |

EXAMPLE 67

N-(3,5-Dichlorobenzyl)N-methyl-2-(1-piperazinyl)-2-indan-carboxamide dihydrochloride The expected product is obtained according to the procedure of Example 4, starting from the compound of Preparation 2 and N-methyl-3,5-dichlorobenzylamine.

Elemental Microanalysis:

|  | % C | % H | % N | % Cl |
| --- | --- | --- | --- | --- |
| Calculated | 53.79 | 5.54 | 8.55 | 28.87 |
| Found | 54.52 | 5.50 | 8.68 | 27.84 |

EXAMPLE 68

(1RS)-N-(3,5Difluorobenzyl)-N-methyl-1-(1-piperazinyl)-1-indan-carboxamide dihydrochloride The expected product is obtained according to the procedure of Example 4, starting from the compound of Preparation 1 and N-methyl-3,5-difluorobenzylamine.

Elemental Microanalysis:

|  | % C | % H | % N | % Cl |
|---|---|---|---|---|
| Calculated | 57.65 | 5.94 | 9.17 | 15.47 |
| Found | 57.73 | 6.29 | 9.06 | 15.71 |

EXAMPLE 69

(1RS)-N-[3-Fluoro-5(trifluoromethyl)benzyl]-N-methyl-1-(1-piperazinyl)-1-indancarboxamide dihydrochloride The expected product is obtained according to the procedure of Example 4, starting from the compound of Preparation 1 and N-methyl-3-fluoro-5-(trifluoromethyl)benzylamine.

Elemental Microanalysis:

|  | % C | % H | % N | % Cl |
|---|---|---|---|---|
| Calculated | 54.34 | 5.35 | 8.27 | 13.95 |
| Found | 53.78 | 5.68 | 8.11 | 14.83 |

EXAMPLE 70

(1RS)-1-[1-(3,5Difluorobenzyloxymethyl)indan-1-yl]piperazine dihydrochloride

The expected product is obtained according to the procedure of Example 1, starting from the compound of Preparation 1 and 3,5-difluorobenzyl bromide.

Elemental Microanalysis:

|  | % C | % H | % N | % Cl |
|---|---|---|---|---|
| Calculated | 58.47 | 6.08 | 6.49 | 16.44 |
| Found | 58.36 | 6.04 | 6.49 | 16.30 |

EXAMPLE 71

N-(3,5Dibromobenzyl)-N-methyl-2-(1-piperazinyl)-2-indan-carboxamide dihydrochloride The expected product is obtained according to the procedure of Example 4, starting from the compound of Preparation 2 and N-methyl-3,5-dibromobenzylamine.

Mass spectrometry: ESI: [M+H]$^+$ m/z 506.0

EXAMPLE 72

N-[3-(Trifluoromethyl)benzyl]-N-methyl-2-(1-piperazinyl)$_2$-indan-carboxamide dihydrochloride The expected product is obtained according to the procedure of Example 4, starting from the compound of Preparation 2 and N-methyl-3-(trifluoromethyl)benzylamine.

Mass spectrometry: ESI: [M+H]$^+$ m/z 418.2

EXAMPLE 73

N-(3,5-Difluorobenzyl)-N-methyl-2-(1-piperazinyl)-2-indan-carboxamide dihydrochloride The expected product is obtained according to the procedure of Example 4, starting from the compound of Preparation 2 and N-methyl-3,5-difluorobenzylamine.

Mass spectrometry: ESI: [M+H]$^+$ m/z 386.2

EXAMPLE 74

N-(3,5-Dimethylbenzyl)-N-methyl-2-(1-piperazinyl)-2-indan-carboxamide dihydrochloride The expected product is obtained according to the procedure of Example 4, starting from the compound of Preparation 2 and N-methyl-3,5-dimethylbenzylamine.

Mass spectrometry: ESI: [M+H]$^+$ m/z 378.3

EXAMPLE 75

N-Benzyl-N-methyl-[2-(1-piperazinyl)indan-2-yl]methanamine trihydrochloride

The expected product is obtained according to the procedure of Example 6, starting from the compound of Example 7.

Mass spectrometry: ESI: [M+H]$^+$ m/z 336.2

EXAMPLE 76

N-[3-Fluoro-5-(trifluoromethyl)benzyl]-2-(1-piperazinyl)-2-indan-carboxamide dihydrochloride The expected product is obtained according to the procedure of Example 4, starting from the compound of Preparation 2 and 3-fluoro-5-(trifluoromethyl)benzylamine.

Elemental Microanalysis:

|  | % C | % H | % N | % Cl |
|---|---|---|---|---|
| Calculated | 53.45 | 5.10 | 8.50 | 14.34 |
| Found | 53.55 | 5.29 | 8.73 | 13.74 |

EXAMPLE 77

N-(3,5Difluorobenzyl)-N-methyl-[2-(1-piperazinyl)indan-2-yl]-methanamine trihydrochloride The expected product is obtained according to the procedure of Example 6, starting from the compound of Example 73.

Elemental Microanalysis:

|  | % C | % H | % N | % Cl |
|---|---|---|---|---|
| Calculated | 54.95 | 6.29 | 8.74 | 22.12 |
| Found | 54.98 | 6.49 | 8.51 | 22.00 |

EXAMPLE 78

N-3,5-(Dimethylbenzyl)-N-methyl-[2-(1-piperazinyl)indan-2-yl]-methanamine trihydrochloride The expected product is obtained according to the procedure of Example 6, starting from the compound of Example 74.

Mass spectrometry: ESI: [M+H]⁺ m/z 364.3

EXAMPLE 79

N-(3,5-Dichlorobenzyl)N-methyl-[2-(1-piperazinyl)indan-2-yl]-methanamine trihydrochloride The expected product is obtained according to the procedure of Example 6, starting from the compound of Example 67.

Mass spectrometry: ESI: [M+H]⁺ m/z 404.2

EXAMPLE 80

N-[3-Fluoro-5-(trifluoromethyl)benzyl]-N-methyl-2-(1-piperazinyl) 2-indancarboxamide dihydrochloride The expected product is obtained according to the procedure of Example 4, starting from the compound of Preparation 2 and N-methyl-3-fluoro-5-(trifluoromethyl)benzylamine.

Mass spectrometry: ESI: [M+H]⁺ m/z 436.2

EXAMPLE 81

N-[3-Fluoro-5-(trifluoromethyl)benzyl]-N-methyl-[2-(1-piperazinyl) indan-2-yl]methanamine dihydrochloride The expected product is obtained according to the procedure of Example 6, starting from the compound of Example 80.

Elemental Microanalysis:

|  | % C | % H | % N | % Cl |
|---|---|---|---|---|
| Calculated | 55.88 | 5.91 | 8.50 | 14.34 |
| Found | 55.50 | 6.32 | 7.98 | 14.47 |

EXAMPLE 82

N-[3-(Trifluoromethyl)benzyl]-N-methyl-[2-(1-piperazinyl)-indan-2-yl]methanamine dihydrochloride The expected product is obtained according to the procedure of Example 6, starting from the compound of Example 72.

Elemental Microanalysis:

|  | % C | % H | % N | % Cl |
|---|---|---|---|---|
| Calculated | 57.99 | 6.35 | 8.82 | 14.88 |
| Found | 57.60 | 6.70 | 8.59 | 14.33 |

EXAMPLE 83

N-[3,5Bis(trifluoromethyl)benzyl]-N-methyl-[2-(1-piperazinyl)-indan-2-yl]methanamine dihydrochloride The expected product is obtained according to the procedure of Example 6, starting from the compound of Example 60.

Elemental Microanalysis:

|  | % C | % H | % N | % Cl |
|---|---|---|---|---|
| Calculated | 52.95 | 5.37 | 7.72 | 13.02 |
| Found | 52.87 | 5.80 | 7.42 | 12.74 |

EXAMPLE 84

(1RS)-N-(3,5-Dibromobenzyl)-N-ethyl-1-(1-piperazinyl)-1-indan-carboxamide dihydrochloride The expected product is obtained according to the procedure of Example 4, starting from the compound of Preparation 1 and N-ethyl-3,5-dibromobenzylamine.

Elemental Microanalysis:

|  | % C | % H | % N | % Cl |
|---|---|---|---|---|
| Calculated | 46.49 | 4.92 | 7.07 | 11.93 |
| Found | 46.42 | 5.16 | 6.96 | 11.59 |

EXAMPLE 85

(1RS)-N-(3,5-Dichlorobenzyl)-N-methyl-1-(1-piperazinyl)-1-indan-carboxamide dihydrochloride The expected product is obtained according to the procedure of Example 4, starting from the compound of Preparation 1 and N-methyl-3,5-dichlorobenzylanine.

Elemental Microanalysis:

|  | % C | % H | % N | % Cl |
|---|---|---|---|---|
| Calculated | 53.79 | 5.54 | 8.55 | 28.87 |
| Found | 54.22 | 5.61 | 8.67 | 29.81 |

EXAMPLE 86

(1α)-N-(3,5Dimethylbenzyl)-1-(1-piperazinyl)-1-indancarboxamide dihydrochloride

Step A: Benzyl (1α)-1-[4-(tert-butyloxycarbonyl)-1-piperazinyl]-1-indancarboxylate.

The expected product is the first of the enantiomers obtained by separation on a chiral HPLC column of the compound obtained in Step A of Example 1.

Step B: (1α)-1-[4-(tert-Butyloxycarbonyl)-1-piperazinyl]-1-indancarboxylic acid.

The expected product is obtained according to the procedure described in Step F of Preparation 1, starting from the compound of Step A above.

Step C: (1α)-N-(3,5-Dimethylbenzyl)-1-(1-piperazinyl)-1-indancarboxamide dihydrochloride The expected product is obtained according to the procedure of Example 4, starting from the compound of Step B above and 3,5-dimethylbenzylamine.

Elemental Microanalysis:

|  | % C | % H | % N | % Cl |
|---|---|---|---|---|
| Calculated | 63.30 | 7.16 | 9.63 | 16.25 |
| Found | 62.93 | 7.30 | 9.50 | 16.40 |

EXAMPLE 87

(1β)-N-(3,5-Dimethylbenzyl)-1-(1-piperazinyl)-1-indancarboxamide dihydrochloride Step A: (1β)-1-[4-(tert-Butyloxycarbonyl)-1-piperazinyl]-1-indancarboxylic acid.

The expected product is obtained according to the procedure described in Step F of Preparation 1, starting from the second of the enantiomers separated in Step A of Example 86.

Step B: (1β)-N-(3,5-Dimethylbenzyl)-1-(1-piperazinyl)-1-indancarboxamide dihydrochloride The expected product is obtained according to the procedure of Example 4, starting from the compound of Step A above and 3,5-dimethylbenzylamine.

Elemental Microanalysis:

|  | % C | % H | % N | % Cl |
|---|---|---|---|---|
| Calculated | 63.30 | 7.16 | 9.63 | 16.25 |
| Found | 63.46 | 7.24 | 9.61 | 16.77 |

EXAMPLE 88

N-(3,5Dibromobenzyl)-N-methyl-[2-(1-piperazinyl)indan-2-yl]-methanamine dihydrochloride The expected product is obtained according to the procedure of Example 6, starting from the compound of Example 71.

Mass spectrometry: ESI: [M+H]$^+$ m/z 492.1

EXAMPLE 89

(1α)-N-[(1α')-1-(3,5-Dimethylphenyl)ethyl]-1-(1-piperazinyl)-1-indancarboxamide dihydrochloride Step A: (1α)-N-[(1RS)-1-(3,5-Dimethylphenyl)ethyl]-1-[4-(tert-butyloxycarbonyl)-1-piperazinyl]-1-indancarboxamide.

The expected product is obtained according to the procedure described in Step A of Example 4, starting from the compound obtained in Step B of Example 86 and (RS)-1-(3,5-dimethylphenyl)ethylamine.

Step B: (1α)-N-[(1α')-1-(3,5-Dimethylphenyl)ethyl]-1-[4-(tert-butyloxycarbonyl)-1-piperazinyl]-1-indancarboxamide The expected product is obtained by chromatography on silica (eluant: dichloromethane/ethyl acetate) of the diastereoisomeric mixture obtained in Step A.

Step C: (1α)-N-[(1α')-1-(3,5-Dimethylphenyl)ethyl]-1-(1-piperazinyl)-1-indan-carboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 63.99 | 7.38 | 9.33 | 15.74 |
| Found | 63.16 | 7.59 | 9.09 | 15.93 |

EXAMPLE 90

(1α)-N-[(1β')-1-(3,5Dimethylphenyl)ethyl]-1-(1-piperazinyl)-1-indancarboxamide dihydrochloride The expected product is obtained according to the procedure described in Step B of Example 4, starting from the second of the diastereoisomers separated in Step B of Example 89.

Elemental Microanalysis:

|  | % C | % H | % N | % Cl |
|---|---|---|---|---|
| Calculated | 63.99 | 7.38 | 9.33 | 15.74 |
| Found | 64.35 | 7.60 | 9.39 | 15.45 |

EXAMPLE 91

(1β)-N-[(1α')-1-(3,5-Dimethylphenyl)ethyl]-1-(1-piperazinyl)-1-indancarboxamide dihydrochloride Step A: (1β)-N-[(1RS)-1-(3,5-Dimethylphenyl)ethyl]-1-[4-(tert-butyloxycarbonyl)-1-piperazinyl]-1-indancarboxamide.

The expected product is obtained according to the procedure described in Step A of Example 4, starting from the compound obtained in Step A of Example 87 and (RS)-1-(3,5-dimethylphenyl)ethylamine.

Step B: (1β)-N-[(1α')-1-(3,5-Dimethylphenyl)ethyl]-1-[4-(tert-butyloxycarbonyl)-1-piperazinyl]-1-indan-carboxamide The expected product is obtained by chromatography on silica (eluant: dichloromethane/ethyl acetate) of the diastereoisomeric mixture obtained in Step A.

Step C: (1β)-N-[(1α')-1-(3,5-Dimethylphenyl)ethyl]-1-(1-piperazinyl)-1-indan-carboxamide dihydrochloride The expected product is obtained according to the procedure described in Step B of Example 4, starting from the compound obtained in Step B above.

Elemental Microanalysis:

|  | % C | % H | % N | % Cl |
| --- | --- | --- | --- | --- |
| Calculated | 63.99 | 7.38 | 9.33 | 15.74 |
| Found | 64.49 | 7.75 | 9.57 | 15.33 |

EXAMPLE 92

(1β)-N-[(1β')-1-(3,5Dimethylphenyl)ethyl]-1-(1-piperazinyl)-1-indancarboxamide dihydrochloride The expected product is obtained according to the procedure described in Step B of Example 4, starting from the second of the diastereoisomers separated in Step B of Example 91.

Elemental Microanalysis:

|  | % C | % H | % N | % Cl |
| --- | --- | --- | --- | --- |
| Calculated | 63.99 | 7.38 | 9.33 | 15.74 |
| Found | 64.00 | 7.66 | 9.31 | 16.13 |

EXAMPLE 93

(1RS)-N-(3,5Dimethylbenzyl)-N-methyl-1-(1-piperazinyl)-1-indan-carboxamide dihydrochloride The expected product is obtained according to the procedure of Example 4, starting from the compound of Preparation 1 and N-methyl-3,5-dimethylbenzylamine.

Elemental Microanalysis:

|  | % C | % H | % N | % Cl |
| --- | --- | --- | --- | --- |
| Calculated | 63.99 | 7.38 | 9.33 | 15.75 |
| Found | 64.79 | 7.38 | 9.57 | 14.78 |

EXAMPLE 94

(1α)N-[(1S)-2-Hydroxy-1-phenylethyl]-1-(1-piperaziny)-1-indan-carboxamide dihydrochloride Step A: (1RS)-N-[(1S)-2-Hydroxy-1-phenylethyl]-1-[4-(tert-butyloxycarbonyl)-1-piperazinyl]-1-indan-carboxamide.

The expected product is obtained according to the procedure described in Step A of Example 4, starting from the compound of Preparation 1 and (S)-2-phenylglycinol.

Step B: (1α)-N-[(1S)-2-Hydroxy-1-phenylethyl]-1-[4-(tert-butyloxycarbonyl)-1-piperazinyl]-1-indan-carboxamide The expected product is obtained by separation, by means of chromatography on silica (eluant: dichloromethane/ethyl acetate), of the diastereoisomeric mixture obtained in Step A Step C: (1α)-N-[(1S)-2-Hydroxy-1-phenylethyl]-1-(1-piperazinyl)-p-indancarboxamide dihydrochloride The expected product is obtained according to the procedure described in Step B of Example 4, starting from the compound obtained in Step B above.

Elemental Microanalysis:

|  | % C | % H | % N | % Cl |
| --- | --- | --- | --- | --- |
| Calculated | 60.27 | 6.67 | 9.58 | 16.17 |
| Found | 59.95 | 6.43 | 9.35 | 16.25 |

EXAMPLE 95

(1β)-N-[1(1S)-2-Hydroxy-1-phenylethyl]-1-(1-piperazinyl)-1-indan-carboxamide dihydrochloride The expected product is obtained according to the procedure described in Step B of Example 4, starting from the second of the diastereoisomers separated in Step B of Example 94.

Elemental Microanalysis:

|  | % C | % H | % N | % Cl |
| --- | --- | --- | --- | --- |
| Calculated | 60.27 | 6.67 | 9.58 | 16.17 |
| Found | 59.95 | 6.64 | 9.50 | 16.42 |

EXAMPLE 96

N-[(1R)-1-(3,5Dimethylphenyl)ethyl]-2-(1-piperazinyl)-2-indan-carboxamide dihydrochloride The expected product is obtained according to the procedure of Example 4, starting from the compound of Preparation 2 and (R)-1-(3,5-dimethylphenyl)ethylamine.

Elemental Microanalysis:

|  | % C | % H | % N | % Cl |
|---|---|---|---|---|
| Calculated | 63.99 | 7.38 | 9.33 | 15.74 |
| Found | 64.34 | 7.04 | 9.45 | 16.22 |

EXAMPLE 97

N-{[2-(1-piperazinyl)indan-2-yl]methyl}-3,5-bis(trifluoromethyl)-benzamide dihydrochloride

Step A: 2-Azidomethyl-2-[4-(tert-butyloxycarbonyl)-1-piperazinyl]-2-indan.

The expected product is obtained by reaction of the compound obtained in Step A of Example 3 with diphenylphosphoryl azide (DPPA) and 1,8-diazabicyclo[5.4.0]undec-7-ene (DBU), according to the procedure described in *J. Org Chem.* 1993, 58, 5886-5888, and then purification by chromatography on silica (eluant: dichloromethane/ethyl acetate 98/2).
IR: $N_3$: 2095 cm$^{-1}$ CO: 1692 cm$^{-1}$

Step B: 2-Aminomethyl-2-[4-(tert-butyloxycarbonyl)-1-piperazinyl]-2-indan.

2.35 mmol of the compound obtained in Step A above are dissolved in 80 ml of tetrahydrofuran, 2.59 mmol of triphenylphosphine are then added and stirring is carried out for ¼ hour. 10 ml of water are then added and stirring is continued for 24 hours. After evaporating off the solvents, the product is purified by chromatography on silica (eluant: dichloromethane/methanol/ammonia 85/15/1) to yield the expected product.

Step C: N-{[2-[4-(tert-Butyloxycarbonyl)-1-piperazinyl]indan-2-yl]methyl}-3,5-bis(trifluoromethyl)benzamide 2 mmol of the amine obtained in Step B above are dissolved in 15 ml of tetrahydrofuran, cooling to 0° C. is then carried out, and a solution of 2 mmol of 3,5-bis(trifluoromethyl)-benzoyl chloride in 5 ml of tetrahydrofuran is added dropwise. Stirring is then carried out for 1 hour, the solvent is evaporated off and the residue is redissolved in methylene chloride and washed successively with sodium bicarbonate solution, with 10% citric acid solution and then with water. After evaporation and chromatography on silica (eluant: dichloromethane/ethyl acetate 98/2), the expected product is recovered.

Step D: N-{[2-(1-piperazinyl)indan-2-yl]methyl}-3,5-bis(trifluoromethyl)benzamide dihydrochloride The expected product is obtained according to the procedure described in Step D of Example 1, starting from the compound obtained in Step C above.

Elemental Microanalysis:

|  | % C | % H | % N | % Cl |
|---|---|---|---|---|
| Calculated | 50.75 | 4.63 | 7.72 | 13.03 |
| Found | 51.52 | 4.84 | 7.72 | 12.72 |

EXAMPLE 98

N-[(1α)-1-(3,5Dibromophenyl)ethyl]-2-(1-piperazinyl)-2-indan-carboxamide dihydrochloride The expected product is obtained according to the procedure of Example 4, starting from the compound of Preparation 2 and (1α)-1-(3,5-dibromophenyl)ethylamine.
Melting point: 178-180° C.

EXAMPLE 99

N-[(1S)-1-(3,5Dimethylphenyl)ethyl]-2-(1-piperazinyl)$_2$-indan-carboxamide dihydrochloride The expected product is obtained according to the procedure of Example 4, starting from the compound of Preparation 2 and (S)-1-(3,5-dimethylphenyl)ethylamine.
Melting point: 175° C.

EXAMPLE 100

N-[(1β)-1-(3,5-Dibromophenyl)ethyl]-2-(1-piperazinyl)$_2$-indan-carboxamide dihydrochloride The expected product is obtained according to the procedure of Example 4, starting from the compound of Preparation 2 and (1β)-1-(3,5-dibromophenyl)ethylamine.
Melting point: 192-194° C.

EXAMPLE 101

(1α)-N-[(1α')-1-(3,5-Bis(trifluoromethyl)phenyl)ethyl]-1-(1-piperazinyl)indancarboxamide dihydrochloride

Step A: (1α')-1-[3,5-Bis(trifluoromethyl)phenyl]ethylamine.

(1RS)-1-[3,5-Bis(trifluoromethyl)phenyl]ethylamine is converted into a salt using (L)-tartaric acid, the mixture of diastereoisomers thereby obtained is separated and then reconversion to the base is carried out on each of the two diastereoisomers. The expected product is the first of the enantiomers thereby obtained.

Step B: (1RS)-N-[(1α')-1-(3,5-Bis(trifluoromethyl)phenyl)ethyl]-1-[4-(tert-butyloxycarbonyl)-1-piperazinyl]-1-indancarboxamide dihydrochloride The expected product is obtained according to the procedure described in Step A of Example 4, starting from Preparation 1 and the compound obtained in Step A above.

Step C: (1α)-N-[(1α')-1-(3,5-Bis(trifluoromethyl)
phenyl)ethyl]-1-[4-(tert-butyloxycarbonyl)-1-piper-
azinyl]-1-indancarboxamide dihydrochloride The expected product is obtained by separation, by means of chromatography on silica (eluant: dichloromethane/ethyl acetate), of the diastereoisomeric mixture obtained in Step B.

Step D: (1α)-N-[(1α')-1-(3,5-Bis(trifluoromethyl)
phenyl)ethyl]-1-(1-piperazinyl)-indancarboxamide
dihydrochloride The expected product is obtained according to the procedure described in Step B of Example 4, starting from the compound obtained in Step C above.

Elemental Microanalysis:

|  | % C | % H | % N | % Cl |
|---|---|---|---|---|
| Calculated | 51.62 | 4.87 | 7.53 | 12.70 |
| Found | 52.46 | 5.10 | 7.50 | 12.06 |

EXAMPLE 102

(1β)-N-[(1α')-1-(3,5-Bis(trifluoromethyl)phenyl)
ethyl]-1-(1-piperazinyl)indancarboxamide dihydro-
chloride The expected product is obtained according to the procedure described in Step B of Example 4, starting from the second of the diastereoisomers separated in Step C of Example 101.

Elemental Microanalysis:

|  | % C | % H | % N | % Cl |
|---|---|---|---|---|
| Calculated | 51.62 | 4.87 | 7.53 | 12.70 |
| Found | 51.97 | 5.00 | 7.38 | 11.79 |

EXAMPLE 103

(1α)-N-[(1β')-1-(3,5Bis(trifluoromethyl)phenyl)
ethyl]-1-(1-piperazinyl)indancarboxamide dihydro-
chloride Step A: (1β')-1-[3,5-Bis(trifluoromethyl)phenyl]
ethylamine.

The expected product is the second of the enantiomers obtained in Step A of Example 101.

Step B: (1RS)-N-[(1β')-1-(3,5-Bis(trifluoromethyl)
phenyl)ethyl]-1-[4-(tert-butyloxycarbonyl)-1-piper-
azinyl]-1-indancarboxamide dihydrochloride The expected product is obtained according to the procedure described in Step A of Example 4, starting from the compound of Preparation 1 and the compound obtained in Step A above.

Step C: (1α)-N-[(1β')-1-(3,5-Bis(trifluoromethyl)
phenyl)ethyl]-1-[4-(tert-butyloxycarbonyl)-1-piper-
azinyl]-1-indancarboxamide dihydrochloride The expected product is obtained by separation, by means of chromatography on silica (eluant: dichloromethane/ethyl acetate), of the diastereoisomeric mixture obtained in Step B Step D: (1α)-N-[(1β')-1-(3,5-Bis(trifluoromethyl)
phenyl)ethyl]-1-(1-piperazinyl)-indancarboxamide
dihydrochloride The expected product is obtained according to the procedure described in Step B of Example 4, starting from the compound obtained in Step C above.

Elemental Microanalysis:

|  | % C | % H | % N | % Cl |
|---|---|---|---|---|
| Calculated | 51.62 | 4.87 | 7.53 | 12.70 |
| Found | 51.05 | 4.68 | 7.24 | 12.25 |

EXAMPLE 104

(1β)-N-[(1β')-1-(3,5-Bis(trifluoromethyl)phenyl)
ethyl]-1-(1-piperazinyl)indancarboxamide dihydro-
chloride The expected product is obtained according to the procedure described in Step B of Example 4, starting from the second of the diastereoisomers separated in Step C of Example 103.

Elemental Microanalysis:

|  | % C | % H | % N | % Cl |
|---|---|---|---|---|
| Calculated | 51.62 | 4.87 | 7.53 | 12.70 |
| Found | 52.43 | 5.16 | 7.52 | 11.94 |

EXAMPLE 105

1-[(1RS)-1-(3-Bromo-5-fluorobenzyloxymethyl)
indan-1-yl]-piperazine dihydrochloride The expected product is obtained according to the procedure of Example 1, starting from the compound of Preparation 1 and 3-bromo-5-fluorobenzyl bromide. Elemental microanalysis:

|  | % C | % H | % N | % Cl |
|---|---|---|---|---|
| Calculated | 51.24 | 5.32 | 5.69 | 14.40 |
| Found | 51.96 | 5.28 | 5.56 | 14.36 |

EXAMPLE 106

1-[(1RS)-1-(3-Chloro-5-fluorobenzyloxymethyl)indan-1-yl]-piperazine dihydrochloride The expected product is obtained according to the procedure of Example 1, starting from the compound of Preparation 1 and 3-chloro-5-fluorobenzyl bromide.

Mass spectrometry: ESI ($H_2O/CH_3CN$): $[M+H]^+$ m/z 375.2 Th

EXAMPLE 107

1-[2-(3,5-Difluorobenzyloxymethyl)indan-2-yl]piperazine dihydrochloride

The expected product is obtained according to the procedure of Example 1, starting from the compound of Preparation 2 and 3,5-difluororobenzyl bromide.

Elemental Microanalysis:

|  | % C | % H | % N | % Cl |
| --- | --- | --- | --- | --- |
| Calculated | 58.47 | 6.08 | 6.49 | 16.44 |
| Found | 58.49 | 6.07 | 6.47 | 17.04 |

EXAMPLE 108

N-[(1S)-1-(3,5-Dimethylphenyl)ethyl]-N-methyl-2-(1-piperazinyl)-2-indancarboxamide dihydrochloride The expected product is obtained according to the procedure of Example 4, starting from the compound of Preparation 2 and N-[(1S)-1-(3,5-dimethylphenyl)ethyl]-N-methylamine.

Elemental Microanalysis:

|  | % C | % H | % N | % Cl |
| --- | --- | --- | --- | --- |
| Calculated | 64.65 | 7.60 | 9.05 | 15.27 |
| Found | 64.66 | 7.66 | 9.29 | 15.18 |

EXAMPLE 109

N-[(1R)-1-(3,5-Dimethylphenyl)ethyl]-N-methyl-2-(1-piperazinyl) 2-indancarboxamide dihydrochloride The expected product is obtained according to the procedure of Example 4, starting from the compound of Preparation 2 and N-[(1R)-1-(3,5-dimethylphenyl)ethyl]-N-methylamine.

Elemental Microanalysis:

|  | % C | % H | % N | % Cl |
| --- | --- | --- | --- | --- |
| Calculated | 64.65 | 7.60 | 9.05 | 15.27 |
| Found | 64.66 | 7.66 | 9.29 | 15.18 |

EXAMPLE 110

1-[2-(3-Bromo-5-fluorobenzyloxymethyl)indan-2-yl]piperazine, dihydrochloride

The expected product is obtained according to the procedure of Example 1, starting from the compound of Preparation 2 and 3-bromo-5-fluorobenzyl bromide.

Elemental Microanalysis:

|  | % C | % H | % N | % Cl |
| --- | --- | --- | --- | --- |
| Calculated | 51.24 | 5.32 | 5.69 | 14.40 |
| Found | 51.37 | 5.33 | 5.67 | 14.72 |

EXAMPLE 111

N-[(1R)-1-(3,5-Dichlorophenyl)ethyl]-2-(1-piperazinyl)-2-indan-carboxamide dihydrochloride The expected product is obtained according to the procedure of Example 4, starting from the compound of Preparation 2 and (1R)-1-(3,5-dichlorophenyl)ethylamine.

Elemental Microanalysis:

|  | % C | % H | % N | % Cl |
| --- | --- | --- | --- | --- |
| Calculated | 53.79 | 5.54 | 8.55 | 28.87 |
| Found | 54.58 | 5.55 | 8.45 | 28.63 |

EXAMPLE 112

1-[2-(3-Fluoro-5-(trifluoromethyl)benzyloxymethyl)indan-2-yl]-piperazine dihydrochloride The expected product is obtained according to the procedure of Example 1, starting from the compound of Preparation 2 and 3-fluoro-5-(trifluoromethyl)benzyl bromide.

Elemental Microanalysis:

|  | % C | % H | % N | % Cl |
| --- | --- | --- | --- | --- |
| Calculated | 54.89 | 5.44 | 5.82 | 14.73 |
| Found | 55.40 | 5.53 | 5.69 | 14.90 |

EXAMPLE 113

N-[(1S)-1-(3,5Bis(trifluoromethyl)phenyl)ethyl]-2-(1-piperazinyl) 2-indancarboxamide dihydrochloride The expected product is obtained according to the procedure of Example 4, starting from the compound of Preparation 2 and (1S)-1-[3,5-bis(trifluoromethyl)phenyl]ethylamine.

Elemental Microanalysis:

|  | % C | % H | % N | % Cl |
|---|---|---|---|---|
| Calculated | 51.62 | 4.87 | 7.53 | 12.70 |
| Found | 51.10 | 4.77 | 7.22 | 12.30 |

EXAMPLE 114

1-[2-(3-Chloro-5-fuorobenzyloxymethyl)indan-2-yl] piperazine dihydrochloride

The expected product is obtained according to the procedure of Example 1, starting from the compound of Preparation 2 and 3-chloro-5-fluorobenzyl bromide.

Elemental Microanalysis:

|  | % C | % H | % N | % Cl |
|---|---|---|---|---|
| Calculated | 56.33 | 5.85 | 6.26 | 23.75 |
| Found | 56.40 | 6.00 | 6.25 | 23.67 |

EXAMPLE 115

(1α)N-[(1α')-1-(3,5-Dibromophenyl)ethyl]-1-(1-piperazinyl) indancarboxamide dihydrochloride Step A: (1α')-1-[3,5-Dibromophenyl]ethylamine.

(1RS)-1-[3,5-Dibromophenyl]ethylamine is converted into a salt using (L)-tartaric acid, the mixture of diastereoisomers thereby obtained is separated and then reconversion to the base is carried out on each of the two diastereoisomers.

The expected product is the first of the enantiomers thereby obtained.

Step B: (1RS)-N-[(1α')-1-(3,5-Dibromophenyl) ethyl]-1-[4-(tert-butyloxycarbonyl)-1-piperazinyl]-1-indancarboxamide dihydrochloride The expected product is obtained according to the procedure described in Step A of Example 4, starting from Preparation 1 and the compound obtained in Step A above.

Step C: (1α)-N-[(1α')-1-(3,5-Dibromophenyl)ethyl]-1-[4-(tert-butyloxycarbonyl)-1-piperazinyl]-1-indancarboxamide dihydrochloride The expected product is obtained by separation, by means of chromatography on silica (eluant: dichloromethane/ethyl acetate), of the diastereoisomeric mixture obtained in Step B.

Step D: (1α)-N-[(1α')-1-(3,5-Dibromophenyl)ethyl]-1-(1-piperazinyl)indan-carboxamide dihydrochloride The expected product is obtained according to the procedure described in Step B of Example 4, starting from the compound obtained in Step C above.

Elemental Microanalysis:

|  | % C | % H | % N | % Cl |
|---|---|---|---|---|
| Calculated | 45.54 | 4.69 | 7.24 | 12.22 |
| Found | 45.94 | 4.77 | 7.02 | 11.32 |

EXAMPLE 116

(1β)-N-[(1α')-1-(3,5-Dibromophenyl)ethyl]-1-(1-piperazinyl) indancarboxamide dihydrochloride The expected product is obtained according to the procedure described in Step B of Example 4, starting from the second of the diastereoisomers separated in Step C of Example 115.

Elemental Microanalysis:

|  | % C | % H | % N | % Cl |
|---|---|---|---|---|
| Calculated | 45.54 | 4.69 | 7.24 | 12.22 |
| Found | 45.58 | 4.80 | 6.98 | 11.64 |

EXAMPLE 117

(1α)-N-[(1β')-1-(3,5-Dibromophenyl)ethyl]-1-(1-piperazinyl)-indancarboxamide dihydrochloride Step A: (1β')-1-[3,5-Dibromophenyl]ethylamine.

The expected product is the second of the enantiomers obtained in Step A of Example 115.

Step B: (1RS)-N-[(1β'-1-(3,5-Dibromophenyl)ethyl]-1-[4-(tert-butyloxycarbonyl)-1-piperazinyl]-1-indancarboxamide dihydrochloride The expected product is obtained according to the procedure described in Step A of Example 4, starting from the compound of Preparation 1 and the compound obtained in Step A above.

Step C: (1α)-N-[(1β')-1-(3,5-Dibromophenyl)ethyl]-1-[4-(tert-butyloxycarbonyl)-1-piperazinyl]-1-indancarboxamide dihydrochloride The expected product is obtained by separation, by means of chromatography on silica (eluant: dichloromethane/ethyl acetate), of the diastereoisomeric mixture obtained in Step B.

Step D: (1α)-N-[(1β')-1-(3,5-Dibromophenyl)ethyl]-1-(1-piperazinyl)indan-carboxamide dihydrochloride The expected product is obtained according to the procedure described in Step B of Example 4, starting from the compound obtained in Step C above.

Elemental Microanalysis:

|  | % C | % H | % N | % Cl |
|---|---|---|---|---|
| Calculated | 45.54 | 4.69 | 7.24 | 12.22 |
| Found | 45.70 | 4.76 | 7.06 | 11.08 |

EXAMPLE 118

(1β)N-[(1β')-1-(3,5Dibromophenyl)ethyl]-1-(1-piperazinyl)-indancarboxamide dihydrochloride The expected product is obtained according to the procedure described in Step B of Example 4, starting from the second of the diastereoisomers separated in Step C of Example 117.

Elemental Microanalysis:

|  | % C | % H | % N | % Cl |
|---|---|---|---|---|
| Calculated | 45.54 | 4.69 | 7.24 | 12.22 |
| Found | 45.53 | 4.56 | 7.10 | 12.08 |

EXAMPLE 119

N-[(1α)-1-(3,5-Dichlorophenyl)ethyl]-N-methyl-2-(1-piperazinyl)-2-indancarboxamide dihydrochloride Step A: N-[(1RS)-1-(3,5-Dichlorophenyl)ethyl]-N-methyl-2-(1-piperazinyl)-2-indan-carboxamide.

The expected product is obtained according to the procedure of Example 4, starting from the compound of Preparation 2 and N-methyl-1-(3,5-dichlorophenyl)ethylamine.

Step B: N-[(1α)-1-(3,5-Dichlorophenyl)ethyl]-N-methyl-2-1-piperazinyl)-2-indan-carboxamide.

The compound obtained in the step above is separated by HPLC chromatography, on a chiral phase, of the racemic compound obtained in the step above.

The expected product is the first of the enantiomers thereby separated.

Step C: N-[(1α)-1-(3,5-Dichlorophenyl)ethyl]-N-methyl-2-(1-piperazinyl)-2-indancarboxamide dihydrochloride The expected product is obtained by conversion of the compound obtained in the step above into a salt using hydrochloric acid.

Elemental Microanalysis:

|  | % C | % H | % N | % Cl |
|---|---|---|---|---|
| Calculated | 54.67 | 5.78 | 8.32 | 14.03 |
| Found | 54.73 | 5.88 | 8.26 | 13.89 |

EXAMPLE 120

N-[(1β)-1-(3,5-Dichlorophenyl)ethyl]-N-methyl-2-(1-piperazinyl)-2-indancarboxamide dihydrochloride The second of the enantiomers separated in Step B of Example 119 is converted into a salt using hydrochloric acid to yield the expected product.

Elemental Microanalysis:

|  | % C | % H | % N | % Cl |
|---|---|---|---|---|
| Calculated | 54.67 | 5.78 | 8.32 | 14.03 |
| Found | 54.95 | 5.96 | 8.15 | 13.41 |

EXAMPLE 121

N-[(1α)-1-(3,5-Difluorophenyl)ethyl]-2-(1-piperazinyl)-2-indan-carboxamide dihydrochloride Step A: N-[(1RS)-1-(3,5-Difluorophenyl)ethyl]-2-1-piperazinyl)-2-indancarboxamide.

The expected product is obtained according to the procedure of Example 4, starting from the compound of Preparation 2 and 1-(3,5-difluorophenyl)ethylamine.

Step B: N-[(1α)-1-(3,5-Difluorophenyl)ethyl]-2-(1-piperazinyl)-2-indancarboxamide.

The compound obtained in the step above is separated by HPLC chromatography, on a chiral phase, of the racemic compound obtained in the step above.

The expected product is the first of the enantiomers thereby separated.

Step C: N-[(1α)-1-(3,5-Difluorophenyl)ethyl]-2-(1-piperazinyl)-2-indancarboxamide dihydrochloride The expected product is obtained by conversion of the compound obtained in the step above into a salt using hydrochloric acid.

Elemental Microanalysis:

|  | % C | % H | % N | % Cl |
|---|---|---|---|---|
| Calculated | 57.65 | 5.94 | 9.17 | 15.47 |
| Found | 57.87 | 5.86 | 9.08 | 15.47 |

EXAMPLE 122

N-[(1β)-1-(3,5-Difluorophenyl)ethyl]-2-(1-piperazinyl)-2-indan-carboxamide dihydrochloride The second of the enantiomers separated in Step B of Example 121 is converted into a salt using hydrochloric acid to yield the expected product.

Elemental Microanalysis:

|  | % C | % H | % N | % Cl |
|---|---|---|---|---|
| Calculated | 57.65 | 5.94 | 9.17 | 15.47 |
| Found | 58.30 | 5.88 | 9.14 | 15.61 |

EXAMPLE 123

(1α)-N-{(1RS)-1-[3,5-Bis(trifluoromethyl)phenyl]ethyl}-N-methyl-1-(1-piperazinyl)-1-indancarboxamide dihydrochloride The expected product is obtained according to the procedure of Example 4, starting from the compound obtained in Step B of Example 86 and (RS)-N-methyl-1-[3,5-bis(trifluoromethyl)phenyl]ethylamine.

Elemental Microanalysis:

|  | % C | % H | % N | % Cl |
|---|---|---|---|---|
| Calculated | 52.46 | 5.11 | 7.34 | 12.39 |
| Found | 52.16 | 5.37 | 6.93 | 11.94 |

EXAMPLE 124

(1β)-N-{(1RS)-1-[3,5-Bis(trifluoromethyl)phenyl]ethyl}-N-methyl-1-(1-piperazinyl)-1-indancarboxamide dihydrochloride The expected product is obtained according to the procedure of Example 4, starting from the compound obtained in Step A of Example 87 and (RS)-N-methyl-1-[3.5-bis(trifluoromethyl)phenyl]ethylamine.

Elemental Microanalysis:

|  | % C | % H | % N | % Cl |
|---|---|---|---|---|
| Calculated | 52.46 | 5.11 | 7.34 | 12.39 |
| Found | 52.99 | 5.15 | 7.20 | 12.21 |

EXAMPLE 125

(1α)-N-[(1α')-1-(3,5-Difluorophenyl)ethyl]-1-(1-piperazinyl)-1-indancarboxamide dihydrochloride Step A: (1α)-N-[(1RS)-1-(3,5-Difluorophenyl)ethyl]-1-[4-(tert-butyloxycarbonyl)-1-piperazinyl]-1-indancarboxamide.

The expected product is obtained according to the procedure described in Step A of Example 4, starting from the compound obtained in Step B of Example 86 and (RS)-1-(3,5-difluorophenyl)ethylamine.

Step B: (1α)-N-[(1α')-1-(3,5-Difluorophenyl)ethyl]-1-[4-(tert-butyloxycarbonyl)-1-piperazinyl]-1-indancarboxamide The expected product is obtained by chromatography on silica (eluant: dichloromethane/ethyl acetate) of the diastereoisomeric mixture obtained in Step A.

Step C: (1α)-N-[(1α')-1-(3,5-Difluorophenyl)ethyl]-1-(1-piperazinyl)-1-indan-carboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 57.65 | 5.94 | 9.17 | 15.47 |
| Found | 57.22 | 6.30 | 8.85 | 15.62 |

EXAMPLE 126

(1α)-N-[(1β')-1-(3,5-Difluorophenyl)ethyl]-1-(1-piperazinyl)-1-indancarboxamide dihydrochloride The expected product is obtained according to the procedure described in Step B of Example 4, starting from the second of the diastereoisomers separated in Step B of Example 125.

Elemental Microanalysis:

|  | % C | % H | % N | % Cl |
|---|---|---|---|---|
| Calculated | 57.65 | 5.94 | 9.17 | 15.47 |
| Found | 57.15 | 6.31 | 8.84 | 15.38 |

EXAMPLE 127

(1β)-N-[(1α')-1-(3,5-Difluorophenyl)ethyl]-1-(1-piperazinyl)-1-indancarboxamide dihydrochloride Step A: (1β)-N-[(1RS)-1-(3,5-Difluorophenyl)ethyl]-1-[4-(tert-butyloxycarbonyl)-1-piperazinyl]-1-indancarboxamide.

The expected product is obtained according to the procedure described in Step A of Example 4, starting from the compound obtained in Step A of Example 87 and (RS)-1-(3,5-difluorophenyl)ethylamine.

Step B: (1β)-N-[(1α')-1-(3,5-Difluorophenyl)ethyl]-1-[4-(tert-butyloxycarbonyl)-1-piperazinyl]-1-indancarboxamide The expected product is obtained by chromatography on silica (eluant: dichloromethane/ethyl acetate) of the diastereoisomeric mixture obtained in Step A.

Step C: (1β)-N-[(1α')-1-(3,5-Difluorophenyl)ethyl]-1-(1-piperazinyl)-1-indan-carboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 57.65 | 5.94 | 9.17 | 15.47 |
| Found | 57.38 | 6.36 | 8.88 | 15.69 |

EXAMPLE 128

(1β)N-[(1β')-1-(3,5-Difluorophenyl)ethyl]-1-(1-piperazinyl)-1-indancarboxamide dihydrochloride The expected product is obtained according to the procedure described in Step B of Example 4, starting from the second of the diastereoisomers separated in Step B of Example 127.

Elemental Microanalysis:

|  | % C | % H | % N | % Cl |
|---|---|---|---|---|
| Calculated | 57.65 | 5.94 | 9.17 | 15.47 |
| Found | 57.38 | 6.33 | 8.87 | 15.34 |

EXAMPLE 129

N-(3-Chloro-5-fluorobenzyl)-2-(1-piperazinyl)$_2$-indancarboxamide dihydrochloride The expected product is obtained according to the procedure of Example 4, starting from the compound of Preparation 2 and 3-chloro-5-fluorobenzylamine.

Elemental Microanalysis:

|  | % C | % H | % N | % Cl |
|---|---|---|---|---|
| Calculated | 54.74 | 5.47 | 9.12 | 15.39 |
| Found | 55.24 | 5.61 | 9.06 | 15.29 |

EXAMPLE 130

N-[(1S)-1-(3,5Dichlorophenyl)ethyl]-2-(1-piperazinyl)-2-indan-carboxamide dihydrochloride The expected product is obtained according to the procedure of Example 4, starting from the compound of Preparation 2 and (1S)-1-[3,5-dichlorophenyl]ethylamine.

Elemental Microanalysis:

|  | % C | % H | % N | % Cl |
|---|---|---|---|---|
| Calculated | 53.79 | 5.54 | 8.55 | 28.87 |
| Found | 54.53 | 5.59 | 8.52 | 28.80 |

EXAMPLE 131

(1α)-N-[(1α')-1-(3,5-Dichlorophenyl)ethyl]-1-(1-piperazinyl)-indancarboxamide dihydrochloride Step A: (1α)-N-[(1RS)-1-(3,5-Dichlorophenyl)ethyl]-1-[4-(tert-butyloxycarbonyl)-1-piperazinyl]-1-indancarboxamide The expected product is obtained according to the procedure described in Step A of Example 4, starting from the compound obtained in Step B of Example 86 and (RS)-1-(3,5-dichlorophenyl)ethylamine.

Step B: (1α)-N-[(1α')-1-(3,5-Dichlorophenyl)ethyl]-1-[4-(tert-butyloxycarbonyl)-1-piperazinyl]-1-indan-carboxamide The expected product is obtained by chromatography on silica (eluant: dichloromethane/ethyl acetate) of the diastereoisomeric mixture obtained in Step A.

Step C: (1α)-N-[(1α')-1-(3,5-Dichlorophenyl)ethyl]-1-(1-piperazinyl)-1-indan-carboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 53.79 | 5.54 | 8.55 | 28.87 |
| Found | 54.21 | 5.69 | 8.04 | 28.87 |

EXAMPLE 132

(1α)N-[(1β')-1-(3,5-Dichlorophenyl)ethyl]-1-(1-piperazinyl)-1-indancarboxamide dihydrochloride The expected product is obtained according to the procedure described in Step B of Example 4, starting from the second of the diastereoisomers separated in Step B of Example 131.

Elemental Microanalysis:

|  | % C | % H | % N | % Cl |
|---|---|---|---|---|
| Calculated | 53.79 | 5.54 | 8.55 | 28.87 |
| Found | 54.26 | 5.40 | 8.04 | 28.03 |

EXAMPLE 133

(1β)-N-[(1α')-1-(3,5-Dichlorophenyl)ethyl]-1-(1-piperazinyl)-1-indancarboxamide dihydrochloride

Step A: (1β)-N-[(1RS)-1-(3,5-Dichlorophenyl)ethyl]-1-[4-(tert-butyloxycarbonyl)-1-piperazinyl]-1-indancarboxamide.

The expected product is obtained according to the procedure described in Step A of Example 4, starting from the compound obtained in Step A of Example 87 and (RS)-1-(3,5-dichlorophenyl)ethylamine.

Step B: (1β)-N-[(1α')-1-(3,5-Dichlorophenyl)ethyl]-1-[4-(tert-butyloxycarbonyl)-1-piperazinyl]-1-indan-carboxamide The expected product is obtained by chromatography on silica (eluant: dichloromethane/ethyl acetate) of the diastereoisomeric mixture obtained in Step A.

Step C: (1β)-N-[(1α')-1-(3,5-Dichlorophenyl)ethyl]-1-(1-piperazinyl)-1-indan-carboxamide dihydrochloride The expected product is obtained according to the procedure described in Step B of Example 4, starting from the compound obtained in Step B above.

Elemental Microanalysis:

|   | % C | % H | % N | % Cl |
|---|---|---|---|---|
| Calculated | 53.79 | 5.54 | 8.55 | 28.87 |
| Found | 54.00 | 5.54 | 8.08 | 28.19 |

EXAMPLE 134

(1β)-N-[(1β')-1-(3,5-Dichlorophenyl)ethyl]-1-(1-piperazinyl)-1-indancarboxamide dihydrochloride The expected product is obtained according to the procedure described in Step B of Example 4, starting from the second of the diastereoisomers separated in Step B of Example 133.

Elemental microanalysis.

|   | % C | % H | % N | % Cl |
|---|---|---|---|---|
| Calculated | 53.79 | 5.54 | 8.55 | 28.87 |
| Found | 53.80 | 5.62 | 7.93 | 27.54 |

EXAMPLE 135

N-(3-Chloro-5-fluorobenzyl)-N-methyl-2-(1-piperazinyl)-2-indan-carboxamide dihydrochloride The expected product is obtained according to the procedure of Example 4, starting from the compound of Preparation 2 and N-methyl-3-chloro-5-fluorobenzylamine.

Elemental Microanalysis:

|   | % C | % H | % N | % Cl |
|---|---|---|---|---|
| Calculated | 55.65 | 5.73 | 8.85 | 22.40 |
| Found | 55.54 | 5.95 | 8.81 | 22.55 |

EXAMPLE 136

N-[(1α)-1-(3,5Difluorophenyl)ethyl]-N-methyl-2-(1-piperazinyl)-2-indancarboxamide dihydrochloride

Step A: N-[(1RS)-1-(3,5-Difluorophenyl)ethyl]-N-methyl-2-(1-piperazinyl)-2-indan-carboxamide.

The expected product is obtained according to the procedure of Example 4, starting from the compound of Preparation 2 and N-methyl-1-(3,5-difluorophenyl)ethylamine.

Step B: N-[(1α)-1-(3,5-Difluorophenyl)ethyl]-N-methyl-2-(1-piperazinyl)-2-indan-carboxamide.

The compound obtained in the step above is separated by HPLC chromatography, on a chiral phase, of the racemic compound obtained in the step above. The expected product is the first of the enantiomers thereby separated.

Step C: N-[(1α)-1-(3,5-Difluorophenyl)ethyl]-N-methyl-2-(1-piperazinyl)-2-indan-carboxamide dihydrochloride The expected product is obtained by conversion of the compound obtained in the step above into a salt using hydrochloric acid.

Elemental Microanalysis:

|   | % C | % H | % N | % Cl |
|---|---|---|---|---|
| Calculated | 58.48 | 6.19 | 8.89 | 15.01 |
| Found | 57.93 | 6.09 | 8.62 | 15.18 |

EXAMPLE 137

N-[(1β)-1-(3,5Difluorophenyl)ethyl]-N-methyl-2-(1-piperazinyl)-2-indancarboxamide dihydrochloride The second of the enantiomers separated in Step B of Example 136 is converted into a salt using hydrochloric acid to yield the expected product.

Elemental Microanalysis:

|   | % C | % H | % N | % Cl |
|---|---|---|---|---|
| Calculated | 58.48 | 6.19 | 8.89 | 15.01 |
| Found | 57.83 | 6.35 | 8.64 | 15.56 |

EXAMPLE 138

(1α)-N-[(1α')-1-(3,5-Dibromophenyl)ethyl]-N-methyl-1-(1-piperazinyl)indancarboxamide dihydrochloride Step A: (1α)-N-[(1RS)-1-(3,5-Dibromophenyl)ethyl]-N-methyl-1-[4-(tert-butyloxy-carbonyl)-1-piperazinyl]-1-indancarboxamide The expected product is obtained according to the procedure described in Step A of Example 4, starting from the compound obtained in Step B of Example 86 and (RS)-N-methyl-1-(3,5-dibromophenyl)ethylamine.

Step B: (1α)-N-[(1α')-1-(3,5-Dibromophenyl)ethyl]-N-methyl-1-[4-(tert-butyloxy-carbonyl)-1-piperazinyl]-1-indancarboxamide The expected product is obtained by chromatography on silica (eluant: dichloromethane/ethyl acetate) of the diastereoisomeric mixture obtained in Step A.

Step C: (1α)-N-[(1α')-1-(3,5-Dibromophenyl)ethyl]-N-methyl-1-(1-piperazinyl)-1-indancarboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 46.49 | 4.92 | 7.07 | 11.93 |
| Found | 46.62 | 5.05 | 6.78 | 11.01 |

EXAMPLE 139

(1α)-N-[(1β')-1-(3,5-Dibromophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 138.

Elemental Microanalysis:

|  | % C | % H | % N | % Cl |
|---|---|---|---|---|
| Calculated | 46.49 | 4.92 | 7.07 | 11.93 |
| Found | 46.14 | 5.05 | 6.65 | 11.14 |

EXAMPLE 140

N-{(1α)-1-[3,5-Bis(trifluoromethyl)phenyl]ethyl}-N-methyl-2-(1-piperazinyl)-2-indancarboxamide dihydrochloride Step A: N-{(1RS)-1-[3,5-Bis(trifluoromethyl)phenyl]ethyl}-N-methyl-2-(1-piperazinyl)-2-indancarboxamide.

The expected product is obtained according to the procedure of Example 4, starting from the compound of Preparation 2 and N-methyl-1-[3,5-bis(trifluoromethyl)phenyl]-ethylamine.

Step B: N-{(1α)-1-[3,5-Bis(trifluoromethyl)phenyl]ethyl}-N-methyl-2-(1-piperazinyl)-2-indancarboxamide The compound obtained in the step above is separated by HPLC chromatography, on a chiral phase, of the racemic compound obtained in the step above.

The expected product is the first of the enantiomers thereby separated.

Step C: N-{(1α)-1-[3,5-Bis(trifluoromethyl)phenyl]ethyl}-N-methyl-2-(1-piperazinyl)-2-indancarboxamide dihydrochloride The expected product is obtained by conversion of the compound obtained in the step above into a salt using hydrochloric acid.

Elemental Microanalysis:

|  | % C | % H | % N | % Cl |
|---|---|---|---|---|
| Calculated | 52.46 | 5.11 | 7.34 | 12.39 |
| Found | 53.00 | 5.39 | 7.20 | 12.03 |

EXAMPLE 141

N-{(1β)-1-[3,5-Bis(trifluoromethyl)phenyl]ethyl}-N-methyl-2-(1-piperazinyl)-2-indancarboxamide hydrochloride The second of the enantiomers separated in Step B of Example 140 is converted into a salt using hydrochloric acid to yield the expected product.

Elemental Microanalysis:

|  | % C | % H | % N | % Cl |
|---|---|---|---|---|
| Calculated | 56.03 | 5.27 | 7.84 | 6.61 |
| Found | 56.54 | 5.44 | 7.66 | 6.49 |

EXAMPLE 142

N-[(1R)-1-Phenylethyl]-N-methyl-2-(1-piperazinyl)-2-indan-carboxamide dihydrochloride The expected product is obtained according to the procedure of Example 4, starting from the compound of Preparation 2 and (1R)-N-methyl-1-phenethylamine.

Elemental Microanalysis:

|  | % C | % H | % N | % Cl |
|---|---|---|---|---|
| Calculated | 63.30 | 7.16 | 9.63 | 16.25 |
| Found | 63.25 | 7.34 | 9.35 | 16.78 |

EXAMPLE 143

N-[(1S)-1-Phenylethyl]-N-methyl-2-(1-piperazinyl)-2-indan-carboxamide dihydrochloride The expected product is obtained according to the procedure of Example 4, starting from the compound of Preparation 2 and (1S)-N-methyl-1-phenethylamine.

Elemental Microanalysis:

|  | % C | % H | % N | % Cl |
|---|---|---|---|---|
| Calculated | 63.30 | 7.16 | 9.63 | 16.25 |
| Found | 63.81 | 7.29 | 9.48 | 16.72 |

EXAMPLE 144

(1α)-N-[(1S)-1-Phenylethyl]-N-methyl-1-(1-piperazinyl)-1-indan-carboxamide dihydrochloride The expected product is obtained according to the procedure of Example 4, starting from the compound obtained in Step B of Example 86 and (1S)-N-methyl-1-phenethylamine.

Elemental Microanalysis:

|  | % C | % H | % N | % Cl |
|---|---|---|---|---|
| Calculated | 63.30 | 7.16 | 9.63 | 16.25 |
| Found | 62.68 | 7.29 | 9.25 | 16.04 |

EXAMPLE 145

(1β)-N-[(1S)-1-Phenylethyl]-N-methyl-1-(1-piperazinyl)-1-indan-carboxamide dihydrochloride The expected product is obtained according to the procedure of Example 4, starting from the compound obtained in Step A of Example 87 and (1S)-N-methyl-1-phenethylamine.

Elemental Microanalysis:

|  | % C | % H | % N | % Cl |
|---|---|---|---|---|
| Calculated | 63.30 | 7.16 | 9.63 | 16.25 |
| Found | 63.51 | 7.54 | 9.47 | 16.06 |

EXAMPLE 146

(1β)-N-[(1R)-1-Phenylethyl]-N-methyl-1-(1-piperazinyl)-1-indan-carboxamide dihydrochloride The expected product is obtained according to the procedure of Example 4, starting from the compound obtained in Step A of Example 87 and (1R)-N-methyl-1-phenethylamine.

Elemental Microanalysis:

|  | % C | % H | % N | % Cl |
|---|---|---|---|---|
| Calculated | 63.30 | 7.16 | 9.63 | 16.25 |
| Found | 63.63 | 7.67 | 9.68 | 15.51 |

EXAMPLE 147

(1α)-N-[(1R)-1-Phenylethyl]-N-methyl-1-(1-piperazinyl)-1-indan-carboxamide dihydrochloride The expected product is obtained according to the procedure of Example 4, starting from the compound obtained in Step B of Example 86 and (1R)-N-methyl-1-phenethylamine.

Elemental Microanalysis:

|  | % C | % H | % N | % Cl |
|---|---|---|---|---|
| Calculated | 63.30 | 7.16 | 9.63 | 16.25 |
| Found | 62.87 | 7.16 | 9.06 | 15.95 |

EXAMPLE 148

N-[(1α)-1-(3,5-Dibromophenyl)ethyl]-N-methyl-2-(1-piperazinyl)-2-indancarboxamide dihydrochloride Step A: N-[(1RS)-1-(3,5-Dibromophenyl)ethyl]-N-methyl-2-(1-piperazinyl)-2-indan-carboxamide The expected product is obtained according to the procedure of Example 4, starting from the compound of Preparation 2 and N-methyl-1-(3,5-dibromophenyl)ethylamine.

Step B: N-[(1α)-1-(3,5-Dibromophenyl)ethyl]-N-methyl-2-1-piperazinyl)-2-indan-carboxamide The compound obtained in the step above is separated by HPLC chromatography, on a chiral phase, of the racemic compound obtained in the step above. The expected product is the first of the enantiomers thereby separated.

Step C: N-[(1α)-1-(3,5-Dibromophenyl)ethyl]-N-methyl-2-(1-piperazinyl)-2-indan-carboxamide dihydrochloride The expected product is obtained by conversion of the compound obtained in the step above into a salt using hydrochloric acid.

Mass spectrometry: [M+H]$^+$=519.1

EXAMPLE 149

N-[(1β)-1-(3,5-Dibromophenyl)ethyl]-N-methyl-2-(1-piperazinyl)-2-indancarboxamide dihydrochloride The second of the enantiomers separated in Step B of Example 148 is converted into a salt using hydrochloric acid to yield the expected product.

Elemental Microanalysis:

|  | % C | % H | % N | % Cl |
|---|---|---|---|---|
| Calculated | 46.49 | 4.92 | 7.07 | 11.93 |
| Found | 46.99 | 4.85 | 6.90 | 11.28 |

EXAMPLE 150

(RS)1-{2-[(1-(3,5-Dimethylphenyl)ethoxy)methyl]indan-2-yl}-piperazine dihydrochloride

Step A: tert-Butyl (RS)-4-(2-{[(3,5-dimethylbenzoyl)oxy]methyl}indan-2-yl)-1-piperazinecarboxylate To 4.8 g of the compound obtained in Step A of Example 3 and 2.16 g of 3,5-dimethyl-benzoic acid dissolved in 10 ml of methylene chloride there are added, at 0° C., 2.76 g of 1-(3-dimethylaminopropyl)-3-ethylcarbodiimide hydrochloride and 150 mg of dimethyl-aminopyridine. After stirring for 20 hours at ambient temperature, the solvent is evaporated off, the residue is redissolved in ethyl acetate, and then the organic phase is washed with water, dried and evaporated. The residue obtained is purified by chromatography on silica gel (eluant: dichloromethane/ethyl acetate 92.5/7.5) to yield the expected product. Melting point: 139° C.

Step B: tert-Butyl 4-[2-({[1-(3,5-dimethylphenyl)vinyl]oxy}methyl)indan-2-yl]-1-piperazinecarboxylate To 4.55 g of the product obtained in the step above, dissolved in 40 ml of tetrahydrofuran, there are added 19.4 ml of a 1M solution of dimethyltitanocene in toluene. The mixture is then heated at reflux under nitrogen. After stirring for 6 hours under reflux, a further 9.7 ml of the titanocene solution are added and refluxing is continued for 18 hours. After returning to ambient temperature, 300 ml of pentane are added and the mixture is filtered. The filtrate is evaporated and the residue is then chromatographed on silica gel (eluant: dichloromethane/ethyl acetate 90/10) to yield the expected product.
Melting point: 128° C.

Step C: tert-Butyl (RS)-4-(2-{[1-(3,5-dimethylphenyl)ethoxy]methyl}indan-2-yl)-1-piperazinecarboxylate To 1.6 g of the product obtained in the step above, dissolved in 40 ml of toluene and 20 ml of anhydrous ethanol, there are added, after degassing, 165 mg (5% molar) of tris(triphenylphosphine)rhodium chloride. The mixture is then hydrogenated for 20 hours at ambient temperature and atmospheric pressure. After evaporating off the solvents and chromatographing on silica gel (eluant: dichloromethane/ethyl acetate 80/20), the expected product is obtained.
IR: >=CO 1688 cm$^{-1}$.

Step D: (RS)-1-{2-[(1-(3,5-Dimethylphenyl)ethoxy)methyl]indan-2-yl}piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 65.90 | 7.83 | 6.40 | 16.21 |
| Found | 66.36 | 8.34 | 6.43 | 15.98 |

EXAMPLE 151

1-{2-[((1α)-1-(3,5-Dichlorophenyl)ethoxy)methyl]indan-2-yl}-piperazine dihydrochloride

Step A: tert-Butyl (RS)-4-(2-{[1-(3,5-dichlorophenyl)ethoxy]methyl}indan-2-yl)-1-piperazinecarboxylate The expected product is obtained according to the procedure described in Steps A to C of Example 150, replacing the 3,5-dimethylbenzoic acid in Step A by 3,5-dichlorobenzoic acid.

Step B: tert-Butyl 4-(2-{[(1α)-1-(3,5-dichlorophenyl)ethoxy]methyl}indan-2-yl)-1-piperazinecarboxylate The compound obtained in the step above is separated by HPLC chromatography, on a chiral phase, of the racemic compound obtained in the step above. The expected product is the first of the enantiomers thereby separated.

Step C: 1-{2-[((1α)-1-(3,5-Dichlorophenyl)ethoxy)methyl]indan-2-yl}piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 55.25 | 5.90 | 5.86 | 29.65 |
| Found | 55.17 | 6.29 | 5.65 | 28.95 |

EXAMPLE 152

1-{2-[((1β)-1-(3,5-Dichlorophenyl)ethoxy)methyl]indan-2-yl}-piperazine dihydrochloride The second of the enantiomers separated in Step B of Example 151 is reacted with hydrochloric acid to yield the expected product.

Elemental Microanalysis:

|  | % C | % H | % N | % Cl |
|---|---|---|---|---|
| Calculated | 55.25 | 5.90 | 5.86 | 29.65 |
| Found | 55.63 | 6.24 | 5.65 | 29.48 |

EXAMPLE 153

1-{(1α)-1-[((1α')-1-(3,5-Difluorophenyl)ethoxy)methyl]indan-1-yl}-piperazine dihydrochloride Step A: (1α)-1-[4-(tert-Butyloxycarbonyl)-1-piperazinyl]-1-hydroxymethylindan.

The expected product is the first of the enantiomers obtained by separation on a chiral HPLC column of the compound obtained in Step B of Example 1.

Step B: tert-Butyl 4-((1α)-1-{[(1RS)-1-(3,5-difluorophenyl)ethoxy]methyl}indan-1-yl)-1-piperazinecarboxylate The expected product is obtained according to the procedure described in Steps A to C of Example 150, starting from the compound obtained in the step above and 3,5-difluorobenzoic acid.

Step C: tert-Butyl 4-((1α)-1-{[((1α')-1-(3,5-difluorophenyl)ethoxy]methyl}indan-1-yl)-1-piperazinecarboxylate The compound obtained in the step above is separated by chromatography on silica. The expected product is the first of the diastereoisomers thereby separated.

Step D: 1-{(1α)-1-[((1α')-1-(3,5-Difluorophenyl)ethoxy)methyl]indan-1-yl}piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 59.33 | 6.34 | 6.29 | 15.92 |
| Found | 60.09 | 6.38 | 5.88 | 16.00 |

EXAMPLE 154

1-{(1α)-1-[((1β')-1-(3,5-Difluorophenyl)ethoxy)methyl]indan-1-yl}-piperazine dihydrochloride The expected product is obtained by reaction of the second of the diastereoisomers separated in Step C of Example 153 with hydrochloric acid.

Elemental Microanalysis:

|  | % C | % H | % N | % Cl |
|---|---|---|---|---|
| Calculated | 59.33 | 6.34 | 6.29 | 15.92 |
| Found | 58.86 | 6.18 | 6.05 | 15.85 |

EXAMPLE 155

1-{(1β)-1-[((1α')-1-(3,5-Difluorophenyl)ethoxy)methyl]indan-1-yl}-piperazine dihydrochloride Step A: (1β)-1-[4-(tert-Butyloxycarbonyl)-1-piperazinyl]-1-hydroxymethylindan.

The expected product is the second of the enantiomers obtained by separation on a chiral HPLC column of the compound obtained in Step B of Example 1.

Step B: tert-Butyl 4-((1β)-1-{[(1RS)-1-(3,5-difluorophenyl)ethoxy]methyl}indan-1-yl)-1-piperazinecarboxylate The expected product is obtained according to the procedure described in Steps A to C of Example 150, starting from the compound obtained in the step above and 3,5-difluorobenzoic acid.

Step C: tert-Butyl 4-((1β)-1-{[((1α')-1-(3,5-difluorophenyl)ethoxy]methyl}indan-1-yl)-1-piperazinecarboxylate The compound obtained in the step above is separated by chromatography on silica. The expected product is the first of the diastereoisomers thereby separated.

Step D: 1-{(1β)-1-[((1α')-1-(3,5-Difluorophenyl)ethoxy)methyl]indan-1-yl}piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 59.33 | 6.34 | 6.29 | 15.92 |
| Found | 58.91 | 6.38 | 6.12 | 16.07 |

EXAMPLE 156

1-{((1β)-1-[(1β')-1-(3,5-Difluorophenyl)ethoxy)methyl]indan-1-yl}-piperazine dihydrochloride The expected product is obtained by reaction of the second of the diastereoisomers separated in Step C of Example 155 with hydrochloric acid.

Elemental Microanalysis:

|  | % C | % H | % N | % Cl |
|---|---|---|---|---|
| Calculated | 59.33 | 6.34 | 6.29 | 15.92 |
| Found | 59.58 | 6.41 | 5.93 | 15.94 |

EXAMPLE 157

1-{2-[((1α)-1-(3,5-Dibromophenyl)ethoxy)methyl]indan-2-yl}-piperazine dihydrochloride Step A: tert-Butyl (RS)-4-(2-{[1-(3,5-dibromophenyl)ethoxy]methyl}indan-2-yl)-j-piperazinecarboxylate The expected product is obtained according to the procedure described in Steps A to C of Example 150, replacing the 3,5-dimethylbenzoic acid in Step A by 3,5-dibromobenzoic acid.

Step B: tert-Butyl 4-(2-{[(1α)-1-(3,5-dibromophenyl)ethoxy]methyl}indan-2-yl)-1-piperazinecarboxylate The compound obtained in the step above is separated by HPLC chromatography, on a chiral phase, of the racemic compound obtained in the step above. The expected product is the first of the enantiomers thereby separated.

Step C: 1-{2-[((1α)-1-(3,5-Dibromophenyl)ethoxy)methyl]indan-2-yl}piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 46.59 | 4.98 | 4.94 | 12.50 |
| Found | 47.21 | 4.73 | 4.95 | 12.54 |

EXAMPLE 158

1-{2-[((1β)-1-(3,5Dibromophenyl)ethoxy)methyl]indan-2-yl}-piperazine dihydrochloride The second of the enantiomers separated in Step B of Example 157 is reacted with hydrochloric acid to yield the expected product.

Elemental Microanalysis:

|  | % C | % H | % N | % Cl |
|---|---|---|---|---|
| Calculated | 46.59 | 4.98 | 4.94 | 12.50 |
| Found | 46.73 | 4.70 | 4.95 | 12.70 |

EXAMPLE 159

1-{(1α)-1-[((1α')-1-[3,5-Bis(trifluoromethyl)phenyl]ethoxy)-methyl]indan-1-yl}piperazine dihydrochloride Step A: tert-Butyl 4-((1α)-1-{[(1RS)-1-[3,5-bis(trifluoromethyl)phenyl]ethoxy]methyl}-indan-1-yl)-1-piperazinecarboxylate The expected product is obtained according to the procedure described in Steps A to C of Example 150, starting from the compound obtained in Step A of Example 153 and 3,5-bis(trifluoromethyl)benzoic acid.

Step B: tert-Butyl 4-((1α)-1-{[(1α')-1-[3,5-bis(trifluoromethyl)phenyl]ethoxy]methyl}-indan-1-yl)-1-piperazinecarboxylate The compound obtained in the step above is separated by chromatography on silica. The expected product is the first of the diastereoisomers thereby separated.

Step C: 1-{(1α)-1-[((1α')-1-[3,5-bis(trifluoromethyl)phenyl]ethoxy)methyl]indan-1-yl}-piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 52.85 | 5.17 | 5.14 | 13.00 |
| Found | 52.93 | 5.38 | 5.00 | 13.11 |

EXAMPLE 160

1-{(1α)-1-[((1β')-1-[3,5-Bis(trifluoromethyl)phenyl]ethoxy)methyl]-indan-1-yl}piperazine dihydrochloride The expected product is obtained by reaction of the second of the diastereoisomers separated in Step B of Example 159 with hydrochloric acid.

Elemental Microanalysis:

|  | % C | % H | % N | % Cl |
|---|---|---|---|---|
| Calculated | 52.85 | 5.17 | 5.14 | 13.00 |
| Found | 53.35 | 5.16 | 5.09 | 12.63 |

EXAMPLE 161

1-{(1β)-1-[((1α')-1-[3,5-Bis(trifluoromethyl)phenyl]
ethoxy)methyl]-indan-1-yl}piperazine dihydrochloride Step A: tert-Butyl 4-((1β)-1-{[(1RS)-1-[3,5-bis(trifluoromethyl)phenyl]ethoxy]methyl}-indan-1-yl)-1-piperazinecarboxylate The expected product is obtained according to the procedure described in Steps A to C of Example 150, starting from the compound obtained in Step A of Example 155 and 3,5-bis(trifluoromethyl)benzoic acid.

Step B: tert-Butyl 4-((1β)-1-{[(1α')-1-[3,5-bis(trifluoromethyl)phenyl]ethoxy]methyl}-indan-1-yl)-1-piperazinecarboxylate The compound obtained in the step above is separated by chromatography on silica. The expected product is the first of the diastereoisomers thereby separated.

Step C: 1-{(1β)-1-[((1α')-1-[3,5-Bis(trifluoromethyl)phenyl]ethoxy)methyl]indan-1-yl}-piperazine dihydrochloride The expected product is obtained by reaction of the compound obtained in the step above with hydrochloric acid.

Elemental Microanalysis:

|  | % C | % H | % N | % Cl |
|---|---|---|---|---|
| Calculated | 52.85 | 5.17 | 5.14 | 13.00 |
| Found | 52.96 | 5.19 | 4.91 | 12.76 |

EXAMPLE 162

1-{(1β)-1-[((1β')-1-[3,5-Bis(trifluoromethyl)phenyl]
ethoxy)methyl]-indan-1-yl}piperazine dihydrochloride The expected product is obtained by reaction of the second of the diastereoisomers separated in Step B of Example 161 with hydrochloric acid.

Elemental Microanalysis:

|  | % C | % H | % N | % Cl |
|---|---|---|---|---|
| Calculated | 52.85 | 5.17 | 5.14 | 13.00 |
| Found | 53.37 | 5.18 | 4.94 | 12.78 |

EXAMPLE 163

(1α)-N-[(1α')-1-(3,5-Difluorophenyl)ethyl]-N-methyl-1-(1-piperazinyl)-1-indancarboxamide dihydrochloride Step A: (1α)-N-[(1RS)-1-(3,5-Difluorophenyl)ethyl]-N-methyl-1-[4-(tert-butyloxy-carbonyl)-1-piperazinyl]-1-indancarboxamide.

The expected product is obtained according to the procedure described in Step A of Example 4, starting from the compound obtained in Step B of Example 86 and (RS)-N-methyl-1-(3,5-difluorophenyl)ethylamine.

Step B: (1α)-N-[(1α')-1-(3,5-Difluorophenyl)ethyl]-N-methyl-1-[4-(tert-butyloxy-carbonyl)-1-piperazinyl]-1-indancarboxamide The expected product is obtained by chromatography on silica (eluant: dichloromethane/ethyl acetate) of the diastereoisomeric mixture obtained in Step A.

Step C: (1α)-N-[(1α')-1-(3,5-Difluorophenyl)ethyl]-N-methyl-1-(1-piperazinyl)-1-indancarboxamide dihydrochloride The expected product is obtained according to the procedure described in Step B of Example 4, starting from the compound obtained in Step B above.

Mass spectrometry ESI/FIA/HR and MS/MS: [M+H]+=400.

EXAMPLE 164

(1α)-N-[(1β')-1-(3,5-Difluorophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 163.

Elemental Microanalysis:

|  | % C | % H | % N | % Cl |
|---|---|---|---|---|
| Calculated | 58.48 | 6.19 | 8.89 | 15.01 |
| Found | 57.89 | 5.96 | 8.43 | 15.40 |

EXAMPLE 165

(1β)-N-[(1α')-1-(3,5-Difluorophenyl)ethyl]-N-methyl-1-(1-piperazinyl)-1-indancarboxamide dihydrochloride Step A: (1β)-N-[(1RS)-1-(3,5-Difluorophenyl)ethyl]-N-methyl-1-[4-(tert-butyloxycarbonyl)-1-piperazinyl]-1-indancarboxamide.

The expected product is obtained according to the procedure described in Step A of Example 4, starting from the compound obtained in Step A of Example 87 and (RS)-N-methyl-1-(3,5-difluorophenyl)ethylamine.

Step B: (1β)-N-[(1α')-1-(3,5-Difluorophenyl)ethyl]-N-methyl-1-[4-(tert-butyloxy-carbonyl)-1-piperazinyl]-1-indancarboxamide The expected product is obtained by chromatography on silica (eluant: dichloromethane/ethyl acetate) of the diastereoisomeric mixture obtained in Step A.

Step C: (1β)-N-[(1α')-1-(3,5-Difluorophenyl)ethyl]-N-methyl-1-(1-piperazillyl)-1-indancarboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 58.48 | 6.19 | 8.89 | 15.01 |
| Found | 58.31 | 5.95 | 8.40 | 14.17 |

EXAMPLE 166

(1β)-N-[(1β')-1-(3,5-Difluorophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 165.
Mass spectrometry ESI/FIA/HR and MS/MS: [M+H]+=400.

EXAMPLE 167

(1β)N-[(1β')-1-(3,5-Dichlorophenyl)ethyl]-N-methyl-1-(1-piperazinyl)-1-indancarboxamide dihydrochloride Step A: (1α)-N-[(1RS)-1-(3,5-Dichlorophenyl)ethyl]-N-methyl-1-[4-(tert-butyloxycarbonyl)-1-piperazinyl]-1-indancarboxamide.

The expected product is obtained according to the procedure described in Step A of Example 4, starting from the compound obtained in Step B of Example 86 and (RS)—N-methyl-1-(3,5-dichlorophenyl)ethylamine.

Step B: (1α)-N-[(1α')-1-(3,5-Dichlorophenyl)ethyl]-N-methyl-1-[4-(tert-butyloxy-carbonyl)-1-piperazinyl]-1-indancarboxamide The expected product is obtained by chromatography on silica (eluant: dichloromethane/ethyl acetate) of the diastereoisomeric mixture obtained in Step A.

Step C: (1α)-N-[(1α')-1-(3,5-Dichlorophenyl)ethyl]-N-methyl-1-(1-piperazinyl)-1-indancarboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 54.67 | 5.78 | 8.32 | 14.03 |
| Found | 55.18 | 5.79 | 8.06 | 12.57 |

EXAMPLE 168

(1α)-N-[(1β')-1-(3,5-Dichlorophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 167.

Elemental Microanalysis:

|  | % C | % H | % N | % Cl |
|---|---|---|---|---|
| Calculated | 54.67 | 5.78 | 8.32 | 14.03 |
| Found | 53.93 | 5.78 | 7.90 | 14.03 |

EXAMPLE 169

(1β)-N-[(1α')-1-(3,5-Dichlorophenyl)ethyl]-N-methyl-1-(1-piperazinyl)-1-indancarboxamide dihydrochloride Step A: (1β)-N-[(1RS)-1-(3,5-Dichlorophenyl)ethyl]-N-methyl-1-[4-(tert-butyloxycarbonyl)-1-piperazinyl]-1-indancarboxamide.

The expected product is obtained according to the procedure described in Step A of Example 4, starting from the compound obtained in Step A of Example 87 and (RS)-N-methyl-1-(3,5-dichlorophenyl)ethylamine.

Step B: (1β)-N-[(1α')-1-(3,5-Dichlorophenyl)ethyl]-N-methyl-1-[4-(tert-butyloxycarbonyl)-1-piperazinyl]-1-indancarboxamide The expected product is obtained by chromatography on silica (eluant: dichloromethane/ethyl acetate) of the diastereoisomeric mixture obtained in Step A.

Step C: (1β)-N-[(1α')-1-(3,5-Dichlorophenyl)ethyl]-N-methyl-1-(1-piperazinyl)-1-indancarboxamide dihydrochloride The expected product is obtained according to the procedure described in Step B of Example 4, starting from the compound obtained in Step B above.
Mass spectrometry ESI/FIA/HR and MS/MS: [M+H]+=432.

EXAMPLE 170

(1β)-N-[(1β')-1-(3,5-Dichlorophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 169.

Mass spectrometry ESI/FIA/HR and MS/MS: [M+H]+=432.

EXAMPLE 171

1-{2-[((1RS)-1-(3,5-Difluorophenyl)ethoxy)methyl]indan-2-yl}-piperazine dihydrochloride The expected product is obtained according to the procedure of Example 150, replacing the 3,5-dimethylbenzoic acid in Step A by 3,5-difluorobenzoic acid.

Elemental Microanalysis:

|  | % C | % H | % N | % Cl |
|---|---|---|---|---|
| Calculated | 59.33 | 6.34 | 6.29 | 15.92 |
| Found | 59.46 | 6.61 | 6.15 | 15.40 |

EXAMPLE 172

1-{2-[((1RS)-1-[3,5-Bis(trifluoromethyl)phenyl]ethoxy)methyl]-indan-2-yl}piperazine dihydrochloride The expected product is obtained according to the procedure of Example 150, replacing the 3,5-dimethylbenzoic acid in Step A by 3,5-bis(trifluoromethyl)benzoic acid.

Elemental Microanalysis:

|  | % C | % H | % N | % Cl |
|---|---|---|---|---|
| Calculated | 52.85 | 5.17 | 5.14 | 13.00 |
| Found | 52.82 | 5.14 | 5.05 | 12.77 |

EXAMPLE 173

1-{2-[((1α)-1-Phenylethoxy)methyl]indan-2-yl}piperazine dihydrochloride

Step A: tert-Butyl (RS)-4-(2-{[1-phenylethoxy]methyl}indan-2-yl)-1-piperazine-carboxylate The expected product is obtained according to the procedure described in Steps A to C of Example 150, replacing the 3,5-dimethylbenzoic acid in Step A by benzoic acid.

Step B: tert-Butyl 4-(2-{[(1α)-1-phenylethoxy]methyl}indan-2-yl)-1-piperazine-carboxylate The compound obtained in the step above is separated by HPLC chromatography, on a chiral phase, of the racemic compound obtained in the step above. The expected product is the first of the enantiomers thereby separated.

Step C: 1-{2-[((1α)-1-Phenylethoxy)methyl]indan-2-yl}piperazine dihydrochloride.

The expected product is obtained by reaction of the compound obtained in the step above with hydrochloric acid.

Elemental Microanalysis:

|  | % C | % H | % N | % Cl |
|---|---|---|---|---|
| Calculated | 64.54 | 7.39 | 6.84 | 17.32 |
| Found | 60.57 | 6.80 | 5.99 | 17.32 |

EXAMPLE 174

1-{2-[((1β)-1-Phenylethoxy)methyl]indan-2-yl}piperazine dihydrochloride

The second of the enantiomers separated in Step B of Example 173 is reacted with hydrochloric acid to yield the expected product.

Elemental Microanalysis:

|  | % C | % H | % N | % Cl |
|---|---|---|---|---|
| Calculated | 64.54 | 7.39 | 6.84 | 17.32 |
| Found | 64.96 | 6.97 | 6.43 | 16.82 |

EXAMPLE 175

1-[(1α)-1-(3,5-Difluorobenzyloxymethyl)indan-1-yl]piperazine dihydrochloride

Step A: (1α)-1-[4-(tert-Butyloxycarbonyl)-1-piperazinyl]-1-hydroxymethylindan.

The expected product is obtained according to the procedure described in Step B of Example 1, starting from the compound obtained in Step A of Example 86.

Step B: 1-[(1α)-1-(3,5-Difluorobenzyloxymethyl)indan-1-yl]piperazine dihydrochloride The expected product is obtained according to the procedure described in Steps C and D of Example 1, starting from the compound obtained in the step above and 3,5-difluorobenzyl bromide.

Elemental Microanalysis:

|  | % C | % H | % N | % Cl |
|---|---|---|---|---|
| Calculated | 58.47 | 6.08 | 6.49 | 16.44 |
| Found | 58.67 | 6.17 | 6.27 | 16.52 |

EXAMPLE 176

1-[(1β)-1-(3,5-Difluorobenzyloxymethyl)indan-1-yl]piperazine dihydrochloride Step A: (1β)-1-[4-(tert-Butyloxycarbonyl)-1-piperazinyl]-1-hydroxymethylindan.

The expected product is obtained according to the procedure described in Step B of Example 1, starting from the second of the enantiomers separated in Step A of Example 86.

Step B: 1-[(1β)-1-(3,5-Difluorobenzyloxymethyl)indan-1-yl]piperazine dihydrochloride The expected product is obtained according to the procedure described in Steps C and D of Example 1, starting from the compound obtained in the step above and 3,5-difluorobenzyl bromide.

Elemental Microanalysis:

|            | % C   | % H  | % N  | % Cl  |
|------------|-------|------|------|-------|
| Calculated | 58.47 | 6.08 | 6.49 | 16.44 |
| Found      | 58.37 | 6.24 | 6.17 | 16.40 |

EXAMPLE 177

(1α)-N-(3,5-Difluorobenzyl)N-methyl-1-(1-piperazinyl)-1-indan-carboxamide dihydrochloride The expected product is obtained according to the procedure of Example 4, starting from the compound obtained in Step B of Example 86 and N-methyl-3,5-difluorobenzylamine.

Elemental Microanalysis:

|            | % C   | % H  | % N  | % Cl  |
|------------|-------|------|------|-------|
| Calculated | 57.65 | 5.94 | 9.17 | 15.47 |
| Found      | 57.21 | 5.99 | 8.36 | 15.47 |

EXAMPLE 178

(1β)-N-(3,5-Difluorobenzyl)-N-methyl-1-(1-piperazinyl-1-indan-carboxamide dihydrochloride The expected product is obtained according to the procedure of Example 4, starting from the compound obtained in Step A of Example 87 and N-methyl-3,5-difluorobenzylamine.

Elemental Microanalysis:

|            | % C   | % H  | % N  | % Cl  |
|------------|-------|------|------|-------|
| Calculated | 57.65 | 5.94 | 9.17 | 15.47 |
| Found      | 58.14 | 6.16 | 8.84 | 14.96 |

EXAMPLE 179

(1α)-N-(3,5Dichlorobenzyl)N-methyl-1-(1-piperazinyl)-1-indan-carboxamide dihydrochloride The expected product is obtained according to the procedure of Example 4, starting from the compound obtained in Step B of Example 86 and N-methyl-3,5-dichlorobenzylamine.

Elemental Microanalysis:

|            | % C   | % H  | % N  | % Cl  |
|------------|-------|------|------|-------|
| Calculated | 53.79 | 5.54 | 8.55 | 28.87 |
| Found      | 53.17 | 6.03 | 8.18 | 29.05 |

EXAMPLE 180

(1β)-N-(3,5-Dichlorobenzyl)-N-methyl-1-(1-piperazinyl)-1-indan-carboxamide dihydrochloride The expected product is obtained according to the procedure of Example 4, starting from the compound obtained in Step A of Example 87 and N-methyl-3,5-dichlorobenzylamine.

Elemental Microanalysis:

|            | % C   | % H  | % N  | % Cl  |
|------------|-------|------|------|-------|
| Calculated | 53.79 | 5.54 | 8.55 | 28.87 |
| Found      | 54.00 | 5.49 | 8.07 | 29.08 |

EXAMPLE 181

(1α)-N-(3-Chloro-5-fluorobenzyl)N-methyl-1-(1-piperazinyl)-1-indancarboxamide dihydrochloride The expected product is obtained according to the procedure of Example 4, starting from the compound obtained in Step B of Example 86 and N-methyl-3-chloro-5-fluorobenzylamine.

Elemental Microanalysis:

|            | % C   | % H  | % N  | % Cl  |
|------------|-------|------|------|-------|
| Calculated | 55.65 | 5.73 | 8.85 | 22.40 |
| Found      | 55.21 | 6.19 | 8.46 | 22.33 |

EXAMPLE 182

(1β)-N-(3-Chloro-5-fluorobenzyl-N-methyl-1-(1-piperazinyl)-1-indancarboxamide dihydrochloride The expected product is obtained according to the procedure of Example 4, starting from the compound obtained in Step A of Example 87 and N-methyl-3-chloro-5-fluorobenzylamine.

Elemental Microanalysis:

|  | % C | % H | % N | % Cl |
|---|---|---|---|---|
| Calculated | 55.65 | 5.73 | 8.85 | 22.40 |
| Found | 55.10 | 6.11 | 8.45 | 22.08 |

EXAMPLE 183

N-[(1α)-1-(3-Chloro-5-fluorophenyl)ethyl]-N-methyl-2-(1-piperazinyl)-2-indancarboxamide hydrochloride Step A: N-[(1RS)-1-(3-Chloro-5-fluorophenyl)ethyl]-N-methyl-2-(1-piperazinyl)-2-indancarboxamide.

The expected product is obtained according to the procedure of Example 4, starting from the compound of Preparation 2 and N-methyl-1-(3-chloro-5-fluorophenyl)ethylamine.

Step B: N-[(1α)-1-(3-Chloro-5-fluorophenyl)ethyl]-N-methyl-2-(1-piperazinyl)-2-indancarboxamide The compound obtained in the step above is separated by HPLC chromatography, on a chiral phase, of the racemic compound obtained in the step above. The expected product is the first of the enantiomers thereby separated.

Step C: N-[(1α)-1-(3-Chloro-5-fluorophenyl)ethyl]-N-methyl-2-(1-piperazinyl)-2-indancarboxamide hydrochloride The expected product is obtained by conversion of the compound obtained in the step above into a salt using hydrochloric acid.

Elemental Microanalysis:

|  | % C | % H | % N | % Cl |
|---|---|---|---|---|
| Calculated | 58.70 | 6.10 | 8.93 | 18.83 |
| Found | 58.82 | 6.22 | 8.81 | 18.73 |

EXAMPLE 184

N-[(1β)-1-(3-Chloro-5-fluorophenyl)ethyl]-N-methyl-2-(1-piperazinyl)-2-indancarboxamide hydrochloride The second of the enantiomers separated in Step B of Example 183 is converted into a salt using hydrochloric acid to yield the expected product.

Elemental Microanalysis:

|  | % C | % H | % N | % Cl |
|---|---|---|---|---|
| Calculated | 58.70 | 6.10 | 8.93 | 18.83 |
| Found | 59.03 | 6.23 | 8.78 | 19.38 |

EXAMPLE 185

(1α)-N-[(1α')-1-(3-Chloro-5-fluorophenyl)ethyl]-N-methyl-1-(1-piperazinyl)-1-indancarboxamide dihydrochloride Step A: (1α)-N-[(1RS)-1-(3-Chloro-5-fluorophenyl)ethyl]-N-methyl-1-[4-(tert-butyloxycarbonyl)-1-piperazinyl]-1-indancarboxamide The expected product is obtained according to the procedure described in Step A of Example 4, starting from the compound obtained in Step B of Example 86 and (RS)-N-methyl-1(3-chloro-5-fluorophenyl)ethylamine.

Step B: (1α)-N-[(1α')-1-(3-Chloro-5-fluorophenyl)ethyl]-N-methyl-1-[4-(tert-butyloxycarbonyl)-1-piperazinyl]-1-indancarboxamide The expected product is obtained by chromatography on silica (eluant: dichloromethane/ethyl acetate) of the diastereoisomeric mixture obtained in Step A.

Step C: (1α)-N-[(1α')-1-(3-Chloro-5-fluorophenyl)ethyl]-N-methyl-1-(1-piperazinyl)-1-indancarboxamide dihydrochloride The expected product is obtained according to the procedure described in Step B of Example 4, starting from the compound obtained in Step B above.

Elemental Microanalysis:

|  | % C | % H | % N | % Cl |
|---|---|---|---|---|
| Calculated | 56.51 | 5.98 | 8.60 | 21.76 |
| Found | 57.14 | 6.01 | 8.47 | 20.75 |

EXAMPLE 186

(1α)-N-[(1β')-1-(3-Chloro-5-fluorophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 185.

Elemental Microanalysis:

|  | % C | % H | % N | % Cl |
|---|---|---|---|---|
| Calculated | 56.51 | 5.98 | 8.60 | 21.76 |
| Found | 57.38 | 5.83 | 8.51 | 20.89 |

EXAMPLE 187

(1β)-N-[(1α')-1-(3-Chloro-5-fluorophenyl)ethyl]-N-methyl-1-(1-piperazinyl)-1-indancarboxamide dihydrochloride Step A: (1β)-N-[(1RS)-1-(3-Chloro-5-fluorophenyl)ethyl]-N-methyl-1-[4-(tert-butyloxycarbonyl)-1-piperazinyl]-1-indancarboxamide The expected product is obtained according to the procedure described in Step A of Example 4, starting from the compound obtained in Step A of Example 87 and (RS)-N-methyl-1-(3-chloro-5-fluorophenyl)ethylamine.

Step B: (1β)-N-[(1α')-1-(3-Chloro-5-fluorophenyl)ethyl]-N-methyl-1-[4-(tert-butyloxycarbonyl)-1-piperazinyl]-1-indancarboxamide The expected product is obtained by chromatography on silica (eluant: dichloromethane/ethyl acetate) of the diastereoisomeric mixture obtained in Step A.

Step C: (1β)-N-[(1α')-1-(3-Chloro-5-fluorophenyl)ethyl]-N-methyl-1-(1-piperazinyl)-1-indancarboxamide dihydrochloride The expected product is obtained according to the procedure described in Step B of Example 4, starting from the compound obtained in Step B above.

Elemental Microanalysis:

|  | % C | % H | % N | % Cl |
| --- | --- | --- | --- | --- |
| Calculated | 56.51 | 5.98 | 8.60 | 21.76 |
| Found | 57.05 | 5.98 | 8.39 | 21.05 |

EXAMPLE 188

(1β)-N-[(1β')-1-(3-Chloro-5-fluorophenyl)ethyl]-N-methyl-1-(1-piperazinyl)-1-indancarboxamide dihydrochloride The expected product is obtained according to the procedure described in Step B of Example 4, starting from the second of the diastereoisomers separated in Step B of Example 187.

Elemental Microanalysis:

|  | % C | % H | % N | % Cl |
| --- | --- | --- | --- | --- |
| Calculated | 56.51 | 5.98 | 8.60 | 21.76 |
| Found | 57.15 | 6.02 | 8.38 | 21.14 |

EXAMPLE 189

N-[3-Chloro-5-fluorobenzyl]-N-methyl-5,6-difluoro-2-(1-piperazinyl)-2-indancarboxamide hydrochloride Step A: 4,5-Difluorophthalic acid 35 g (0.161 mol) of 4,5-dichlorophthalic anhydride, 32.7 g of potassium fluoride and 140 ml of sulpholane are introduced into an autoclave. The reaction mixture is then heated at 180° C. for 24 hours and is then, after returning to ambient temperature, poured into 500 ml of 1N sodium hydroxide solution and washed 3 times with ether. The aqueous phase is acidified to pH=1 using hydrochloric acid and is then extracted with ether. The ether phase is washed with water, dried and evaporated to yield the expected product.

Step B: (4,5-Difluoro-2-hydroxymethylphenyl)methanol

To a solution of 0.198 mol of sodium borohydride in, 150 ml of tetrahydrofuran there is added, over 20 minutes and maintaining the temperature at 20° C., a solution of 8.25 mmol of the compound obtained in the step above in 150 ml of tetrahydrofuran. After stirring for 3 hours at ambient temperature, there is added, over 30 minutes and maintaining the temperature at 20° C., a solution of 8.25 mmol of iodine in 150 ml of tetrahydrofuran. After stirring overnight at ambient temperature, the reaction mixture is cooled using an iced water bath and then 45 ml of 3N hydrochloric acid are added dropwise. After stirring for a further 30 minutes, ethyl ether is added. The insoluble matter that forms is filtered off. The ether and tetrahydrofuran are then evaporated off, ethyl ether is added and then the solution obtained is washed with a 1N solution of sodium thiosulphate, with 3N sodium hydroxide solution and then with water to yield, after drying and evaporation, the expected product.

Step C: 1,2-Bis-bromomethyl-4,5-difluorobenzene

To 0.195 mol of the compound obtained in the step above in 1.25 litres of ether there is added, dropwise, over 1 hour 30 minutes, a solution of 0.916 mol of phosphorus tribromide in 300 ml of ether. The reaction mixture is then stirred overnight at ambient temperature; it is subsequently poured into 1 litre of ice-cold water and separated. The organic phase is then washed with 1N sodium hydroxide solution and then with water and finally with saturated sodium chloride solution before being dried and concentrated to yield the expected product.

Step D: 2-(Benzhydrylidene-amino)-5,6-difluoroindan-2-carboxylic acid ethyl ester To 0.374 mol of sodium hydride 95% in 160 ml of tetrahydrofuran there is added, over 40 minutes and maintaining the temperature of the reaction mixture below 5° C., a solution of 0.17 mol of the compound obtained in the step above and 0.17 mol of (benzhydrylidene-amino)acetic acid ethyl ester in 300 ml of tetrahydrofuran. After stirring overnight at ambient temperature, the reaction mixture is filtered and concentrated to yield the expected product.

Step E: Ethyl 2-amino-5,6-difluoro-2-indancarboxylate hydrochloride

To 0.17 mol of the compound obtained in the step above, dissolved in 500 ml of dioxane, there are added 510 ml of 1N hydrochloric acid, and then the reaction mixture is stirred overnight at ambient temperature. The dioxane is then evaporated off; the residue obtained is subsequently made solid by stirring up with 1.5 litres of ether and is filtered off, washed and then dried to yield the expected product.

Step F: 2-[4-(tert-Butyloxycarbonyl)-1-piperazinyl]-5,6-difluoro-2-indan-carboxylic acid The expected product is obtained according to the procedure described in Steps C to F of Preparation 1, starting from the compound obtained in the step above.

Step G: N-[3-Chloro-5-fluorobenzyl]-N-methyl-5,6-difluoro-2-(1-piperazinyl)-2-indancarboxamide hydrochloride The expected product is obtained according to the procedure of Example 4, starting from the compound obtained in the step above and N-methyl-3-chloro-5-fluorobenzylamine.

Elemental Microanalysis:

|  | % C | % H | % N | % Cl |
|---|---|---|---|---|
| Calculated | 55.71 | 5.10 | 8.86 | 14.95 |
| Found | 55.85 | 5.43 | 9.03 | 15.61 |

EXAMPLE 190

N-(3-Chloro-5-fluorobenzyl)-N-methyl-2-(1-piperazinyl)-2,3-dihydro-1H-cyclopenta[b]naphthalene-2-carboxamide hydrochloride Step A: 2,3-Bis(bromomethyl)naphthalene To 0.454 mol of 2,3-dimethyl-naphthalene in 710 ml of carbon tetrachloride there are added 0.953 mol of N-bromosuccinimide and 45.4 mmol of 2,2'-azobisisobutyronitrile. The reaction mixture is then heated at 65° C. for 4 hours and subsequently concentrated and purified by chromatography on silica gel, using a gradient of cyclohexane and dichloromethane (cyclohexane/dichloromethane: 70/30 to 0/100) as eluant, to yield the expected product.

Step B: Ethyl 2-amino-2,3-dihydro-1H-cyclopenta[b]naphthalene-2-carboxylate hydrochloride The expected product is obtained according to the procedure described in Steps D to E of Example 189, starting from the compound obtained in the step above.

Step C: 2-[4-(tert-Butoxycarbonyl)-1-piperazinyl]-2,3-dihydro-1H-cyclopenta[b]-naphthalene-2-carboxylic acid The expected product is obtained according to the procedure described in Steps C to F of Preparation 1, starting from the compound obtained in the step above.

Step D: N-(3-Chloro-5-fluorobenzyl)-N-methyl-2-(1-piperazinyl)-2,3-dihydro-1H-cyclopenta[b]naphthalene-2-carboxamide hydrochloride The expected product is obtained according to the procedure of Example 4, starting from the compound obtained in the step above and N-methyl-3-chloro-5-fluorobenzylamine.

Elemental Microanalysis:

|  | % C | % H | % N | % Cl |
|---|---|---|---|---|
| Calculated | 63.94 | 5.78 | 8.60 | 7.26 |
| Found | 63.56 | 5.58 | 8.23 | 8.15 |

EXAMPLE 191

N-[3-Chloro-5-fluorobenzyl]-N-methyl-5,6-dichloro-2-(1-piperazinyl)-2-indancarboxamide hydrochloride Step A: 4,5-Dichlorophthalic acid The expected product is obtained by ring-opening of 4,5-dichlorophthalic anhydride using acetic anhydride.

Step B: Ethyl 2-amino-5,6-dichloro-2-indancarboxylate hydrochloride

The expected product is obtained according to the procedure described in Steps B to E of Example 189, starting from the compound obtained in the step above.

Step C: 2-[4-(tert-Butyloxycarbonyl)-1-piperazinyl]-5,6-dichloro-2-indancarboxylic acid The expected product is obtained according to the procedure described in Steps C to F of Preparation 1, starting from the compound obtained in the step above.

Step D: N-[3-Chloro-5-fluorobenzyl]-N-methyl-5,6-dichloro-2-(1-piperazinyl)-2-indancarboxamide hydrochloride The expected product is obtained according to the procedure of Example 4, starting from the compound obtained in the step above and N-methyl-3-chloro-5-fluorobenzylamine.

Elemental Microanalysis:

|  | % C | % H | % N | % Cl |
|---|---|---|---|---|
| Calculated | 52.09 | 4.77 | 8.28 | 27.96 |
| Found | 52.77 | 4.65 | 8.21 | 28.83 |

EXAMPLE 192

1-[(1α)-1-(3,5-Difluorobenzyloxymethyl)-5,6-difluoroindan-1-yl]-piperazine dihydrochloride Step A: 3-(3,4-Difluorophenyl)propionyl chloride To 0.27 mol of 3,4-difluorocinnamic acid dissolved in dichloroethane there are added 20 drops of dimethylformamide and 100 ml of thionyl chloride.

The mixture is then heated at reflux for 5 hours, and is subsequently evaporated to dryness and dried to yield the expected product.

Step B: 5,6-Difluoro-1-indanone

To 58 g of the acid chloride obtained in the step above, dissolved in dichloroethane, there are added, at 0° C., over 10 minutes and in 3 portions, 51.3 g of aluminium chloride. After stirring at 0° C. for 40 minutes, the solution is poured into 600 ml of ice-cold 1N hydrochloric acid.

The mixture is then separated, washed twice with 1N sodium hydroxide solution and then with water and with brine, before being dried, filtered, evaporated and dried to yield the expected product.

Step C: (1RS)-1-Amino-5,6-difluoro-1-indancarboxylic acid

To 0.27 mol of the compound obtained in the step above in 650 ml of ethanol and 50 ml of water there are added 113.6 g of ammonium carbonate and then 35.8 g of potassium cyanide.

The reaction mixture is then heated at 120° C. under pressure for 3 hours (the pressure increases to 20 bars).

After cooling, the solvents are evaporated off and the residue is taken up in water. The insoluble material is filtered off and dried.

The hydantoin thereby obtained is heated in the autoclave for 9 hours at 120° C. in 1.4 litres of water, in the presence of 0.17 mol of barium hydroxide.

After cooling, the mixture is filtered; finely divided dry ice (solid carbon dioxide) is added to the filtrate to adjust to pH 7. The mixture is filtered, and then the filtrate is evaporated to dryness to yield the expected product.

Step D: (1RS)-1-[(tert-Butyloxycarbonyl)amino]-5,6-difluoro-1-indancarboxylic acid To 0.17 mol of the compound obtained in the step above in 1.3 litres of dioxane there are added 398 ml of 1N sodium hydroxide solution and then, at 0-5° C., 0.23 mol of di(tert-butyl) dicarbonate dissolved in 100 ml of dioxane.

After stirring for 48 hours at ambient temperature, the dioxane is evaporated off and the residue is taken up in 425 ml of 1N hydrochloric acid.

The solution is then saturated with sodium chloride and extracted with ethyl acetate.

The organic phases are dried, filtered and evaporated to yield the expected product.

Step E: (1RS)-1-[4-(tert-Butyloxycarbonyl)-1-piperazinyl]-5,6-difluoro-1-indan-carboxylic acid The expected compound is obtained according to the procedure of Preparation 1, starting from the compound obtained in the step above.

Step F: Benzyl (1RS)-1-[4-(tert-butyloxycarbonyl)-1-piperazinyl]-5,6-difluoro-1-indancarboxylate The expected compound is obtained according to the procedure described in Step A of Example 1, starting from the compound obtained in the step above.

Step G: Benzyl (1α)-1-[4-(tert-butyloxycarbonyl)-1-piperazinyl]-5,6-difluoro-1-indancarboxylate The expected product is obtained by separation on a chiral HPLC column of the compound obtained in the step above.

Step H: 1-[(1α)-1-(3,5-Difluorobenzyloxymethyl)-5,6-difluoroindan-1-yl]piperazine dihydrochloride The expected compound is obtained according to the procedure described in Steps B to D of Example 1, starting from the compound obtained in the step above and 3,5-difluorobenzyl bromide.

Elemental Microanalysis:

|  | % C | % H | % N | % Cl |
|---|---|---|---|---|
| Calculated | 53.97 | 5.18 | 5.99 | 15.17 |
| Found | 54.21 | 5.26 | 5.56 | 14.90 |

EXAMPLE 193

1-[(1β)-1-(3,5-Difluorobenzyloxymethyl)-5,6-difluoroindan-1-yl]-piperazine dihydrochloride

Step A: Benzyl (1β)-1-[4-(tert-butyloxycarbonyl)-1-piperazinyl]-5,6-difluoro-1-indancarboxylate The expected product is the second of the enantiomers separated in Step G of Example 192.

Step B: 1-[(1β)-1-(3,5-Difluorobenzyloxymethyl)-5,6-difluoroindan-1-yl]piperazine dihydrochloride The expected compound is obtained according to the procedure described in Steps B to D of Example 1, starting from the compound obtained in the step above and 3,5-difluorobenzyl bromide.

Elemental Microanalysis:

|  | % C | % H | % N | % Cl |
|---|---|---|---|---|
| Calculated | 53.97 | 5.18 | 5.99 | 15.17 |
| Found | 53.26 | 5.53 | 6.44 | 15.69 |

EXAMPLE 194

1-[(1α)-1-(3,5-Difluorobenzyloxymethyl)-5,6-dichloroindan-1-yl]-piperazine hydrochloride

Step A: Benzyl (1RS)-1-[4-(tert-butyloxycarbonyl)-1-piperazinyl]-5,6-dichloro-1-indancarboxylate The expected compound is obtained according to the procedure described in Steps A to F of Example 192, replacing the 3,4-difluorocinnamic acid in Step A by 3,4-dichloro-cinnamic acid.

Step B: Benzyl (1α)-1-[4-(tert-butyloxycarbonyl)-1-piperazinyl]-5,6-dichloro-1-indancarboxylate The expected product is obtained by separation on a chiral HPLC column of the compound obtained in the step above.

Step C: 1-[(1α)-1-(3,5-Difluorobenzyloxymethyl)-5,6-dichloroindan-1-yl]piperazine hydrochloride The expected compound is obtained according to the procedure described in Steps B to D of Example 1, starting from the compound obtained in the step above and 3,5-difluorobenzyl bromide.

Elemental Microanalysis:

|  | % C | % H | % N |
| --- | --- | --- | --- |
| Calculated | 54.39 | 5.00 | 6.04 |
| Found | 54.97 | 5.08 | 5.71 |

EXAMPLE 195

1-[(1β)-1-(3,5Difluorobenzyloxymethyl)-5,6-difluoroindan-1-yl]-piperazine hydrochloride Step A: Benzyl (1β)-1-[4-(tert-butyloxycarbonyl)-1-piperazinyl]-5,6-dichloro-1-indancarboxylate The expected product is the second of the enantiomers separated in Step B of Example 194.

Step B: 1-[(1β)-1-(3,5-Difluorobenzyloxymethyl)-5,6-dichloroindan-1-yl]piperazine hydrochloride The expected compound is obtained according to the procedure described in Steps B to D of Example 1, starting from the compound obtained in the step above and 3,5-difluorobenzyl bromide.

Elemental Microanalysis:

|  | % C | % H | % N | % Cl |
| --- | --- | --- | --- | --- |
| Calculated | 54.39 | 5.00 | 6.04 | 22.93 |
| Found | 54.54 | 5.04 | 5.69 | 22.89 |

EXAMPLE 196

1-[(1α)-1-(3-Bromo-5-fluorobenzyloxymethyl)indan-1-yl]-piperazine dihydrochloride The expected product is obtained according to the procedure described in Steps B to D of Example 1, starting from the compound obtained in Step A of Example 175 and 3-bromo-5-fluorobenzyl bromide.

Elemental Microanalysis:

|  | % C | % H | % N | % Cl |
| --- | --- | --- | --- | --- |
| Calculated | 51.24 | 5.32 | 5.69 | 14.40 |
| Found | 51.36 | 5.35 | 5.46 | 14.51 |

EXAMPLE 197

1-[(1β)-1-(3-Bromo-5-fluorobenzyloxymethyl)indan-1-yl]-piperazine dihydrochloride The expected product is obtained according to the procedure described in Steps B to D of Example 1, starting from the compound obtained in Step A of Example 176 and 3-bromo-5-fluorobenzyl bromide.

Elemental Microanalysis:

|  | % C | % H | % N | % Cl |
| --- | --- | --- | --- | --- |
| Calculated | 51.24 | 5.32 | 5.69 | 14.40 |
| Found | 51.65 | 5.38 | 5.64 | 14.44 |

EXAMPLE 198

N-(3-Fluorobenzyl)-N-methyl-2-(1-piperazinyl)-2-indan-carboxamide dihydrochloride The expected product is obtained according to the procedure of Example 4, starting from the compound of Preparation 2 and N-methyl-3-fluorobenzylamine.

EXAMPLE 199

N-(3-Chlorobenzyl)-N-methyl-2-(1-piperazinyl)-2-indan-carboxamide dihydrochloride The expected product is obtained according to the procedure of Example 4, starting from the compound of Preparation 2 and N-methyl-3-chlorobenzylamine.

EXAMPLE 200

N-(3-Bromobenzyl)-N-methyl-2-(1-piperazinyl)-2-indan-carboxamide dihydrochloride The expected product is obtained according to the procedure of Example 4, starting from the compound of Preparation 2 and N-methyl-3-bromobenzylamine.

EXAMPLE 201

N-Methyl-N-[3-(trifluoromethyl)benzyl]-2-(1-piperazinyl)-2-indancarboxamide dihydrochloride The expected product is obtained according to the procedure of Example 4, starting from the compound of Preparation 2 and N-methyl-3-(trifluoromethyl)benzylamine.

EXAMPLE 202

N-(3-Chloro-5-fluoro-2-methoxybenzyl)-N-methyl-2-(1-piperazinyl)-2-indancarboxamide dihydrochloride The expected product is obtained according to the procedure of Example 4, starting from the compound of Preparation 2 and N-methyl-3-chloro-5-fluoro-2-methoxybenzylamine.

EXAMPLE 203

N-(5Chloro-3-fluoro-2-methoxybenzyl)-N-methyl-2-(1-piperazinyl)-2-indancarboxamide dihydrochloride The expected product is obtained according to the procedure of Example 4, starting from the compound of Preparation 2 and N-methyl-5-chloro-3-fluoro-2-methoxybenzylamine.

EXAMPLE 204

N-(3-Chloro-5-fluoro-4-methoxybenzyl)-N-methyl-2-(1-piperazinyl)-2-indancarboxamide dihydrochloride The expected product is obtained according to the procedure of Example 4, starting from the compound of Preparation 2 and N-methyl-3-chloro-5-fluoro-4-methoxybenzylamine.

EXAMPLE 205

N-(3,5-Difluoro-2-methoxybenzyl)-N-methyl-2-(1-piperazinyl)-2-indancarboxamide dihydrochloride The expected product is obtained according to the procedure of Example 4, starting from the compound of Preparation 2 and N-methyl-3,5-difluoro-2-methoxybenzylamine.

EXAMPLE 206

N-(3,5-Difluoro-4-methoxybenzyl)-N-methyl-2-(1-piperazinyl)-2-indancarboxamide dihydrochloride The expected product is obtained according to the procedure of Example 4, starting from the compound of Preparation 2 and N-methyl-3,5-difluoro-4-methoxybenzylamine.

EXAMPLE 207

N-(3,5-Dichloro-2-methoxybenzyl)-N-methyl-2-(1-piperazinyl)-2-indancarboxamide dihydrochloride The expected product is obtained according to the procedure of Example 4, starting from the compound of Preparation 2 and N-methyl-3,5-dichloro-2-methoxybenzylamine.

EXAMPLE 208

N-(3,5-Dichloro-4-methoxybenzyl)-N-methyl-2-(1-piperazinyl)-2-indancarboxamide dihydrochloride The expected product is obtained according to the procedure of Example 4, starting from the compound of Preparation 2 and N-methyl-3,5-dichloro-4-methoxybenzylamine.

EXAMPLE 209

N-(3-Cyanobenzyl)-N-methyl-2-(1-piperazinyl)-2-indan-carboxamide dihydrochloride The expected product is obtained according to the procedure of Example 4, starting from the compound of Preparation 2 and N-methyl-3-cyanobenzylamine.

EXAMPLE 210

N-(3-Cyano-5-fluorobenzyl)-N-methyl-2-(1-piperazinyl)-2-indan-carboxamide dihydrochloride The expected product is obtained according to the procedure of Example 4, starting from the compound of Preparation 2 and N-methyl-3-cyano-5-fluorobenzylamine.

EXAMPLE 211

N-(3-Chloro-5-cyanobenzyl)-N-methyl-2-(1-piperazinyl)-2-indan-carboxamide dihydrochloride The expected product is obtained according to the procedure of Example 4, starting from the compound of Preparation 2 and N-methyl-3-chloro-5-cyanobenzylamine.

EXAMPLE 212

N-[(2,6-Difluoro-4-pyridyl)methyl]-N-methyl-2-(1-piperazinyl)-2-indancarboxamide dihydrochloride The expected product is obtained according to the procedure of Example 4, starting from the compound of Preparation 2 and N-[(2,6-difluoro-4-pyridyl)methyl]-N-methylamine.

EXAMPLE 213

N-[(2-Chloro-6-fluoro-4-pyridyl)methyl]-N-methyl-2-(1-piperazinyl)-2-indancarboxamide dihydrochloride The expected product is obtained according to the procedure of Example 4, starting from the compound of Preparation 2 and N-[(2-chloro-6-fluoro-4-pyridyl)methyl]-N-methylamine.

EXAMPLE 214

N-[(2,6-Dichloro-4-pyridyl)methyl]-N-methyl-2-(1-piperazinyl)-2-indancarboxamide dihydrochloride The expected product is obtained according to the procedure of Example 4, starting from the compound of Preparation 2 and N-[(2,6-dichloro-4-pyridyl)methyl]-N-methylamine.

EXAMPLE 215

N-[(4,6-Difluoro-2-pyridyl)methyl]-N-methyl-2-(1-piperazinyl)-2-indancarboxamide dihydrochloride The expected product is obtained according to the procedure of Example 4, starting from the compound of Preparation 2 and N-[(4,6-difluoro-2-pyridyl)methyl]-N-methylamine.

EXAMPLE 216

N-[(6-Chloro-4-fluoro-2-pyridyl)methyl]-N-methyl-2-(1-piperazinyl)-2-indancarboxamide dihydrochloride The expected product is obtained according to the procedure of Example 4, starting from the compound of Preparation 2 and N-[(6-chloro-4-fluoro-2-pyridyl)methyl]-N-methylamine.

EXAMPLE 217

N-[(4,6-Dichloro-2-pyridyl)methyl]-N-methyl-2-(1-piperazinyl)-2-indancarboxamide dihydrochloride The expected product is obtained according to the procedure of Example 4, starting from the compound of Preparation 2 and N-[(4,6-dichloro-2-pyridyl)methyl]-N-methylamine.

EXAMPLE 218

N-[(4-Chloro-6-fluoro-2-pyridyl)methyl]-N-methyl-2-(1-piperazinyl)-2-indancarboxamide dihydrochloride The expected product is obtained according to the procedure of Example 4, starting from the compound of Preparation 2 and N-[(4-chloro-6-fluoro-2-pyridyl)methyl]-N-methylamine.

Pharmacological Study of Compounds of the Invention

EXAMPLE 219

Determination of the Affinity for Serotonin Reuptake Sites in the Rat

The affinity of the compounds for the serotonin (5-HTT) reuptake site is evaluated by competition experiments with [$^3$H]-citalopram on rat frontal cortex membranes. The cortices are homogenised using a Polytron in 40 volumes (weight/volume) of cold Tris-HCl (50 mM, pH 7.4) incubation buffer containing 120 mM NaCl and 5 mM KCl and are then centrifuged for a first time. The sediment is resuspended in the same buffer, incubated for 10 minutes at 37° C. and then re-centrifuged. The membranes are washed a further two times and the sediment is then resuspended in an appropriate volume of incubation buffer. The membranes are then incubated for 2 hours at 25° C. with the compound under test in the presence of 0.7 nM [$^3$H]-citalopram. Non-specific binding is determined with 10 μM fluoxetine. At the end of the incubation period, the samples are filtered through Unifilter GF/B type filters pretreated with PEI (0.5%) and washed several times with the incubation buffer. The radioactivity retained on the filters is counted after addition of scintillation liquid, with the aid of a scintillation counter. The isotherms obtained are analysed by non-linear regression to determine the IC$_{50}$ values, which are converted into K$_i$ using the Cheng-Prusoff equation:

$$K_i = IC_{50}/(1+L/Kd)$$

wherein L represents the concentration of radioligand and Kd is the dissociation constant of [$^3$H]-citalopram on the serotonin reuptake site (0.7 nM). The results are expressed as pK$_i$=−log K$_i$.

The results obtained for representative compounds of the invention are collated in the following table:

| Compound | pKi r5-HTT |
|---|---|
| Example 1 | 6.61 |
| Example 2 | 7.27 |
| Example 3 | 7.20 |
| Example 68 | 7.47 |
| Example 69 | 6.82 |
| Example 70 | 8.49 |
| Example 85 | 7.03 |
| Example 135 | 7.36 |

EXAMPLE 220 hNK$_1$ Binding

The affinity of compounds of the invention was determined by competition experiments in the presence of [$^3$H]-Substance P (Sar-9, MetO2-11,2-propyl-3,4-3H). IM9 human lymphoblast cells endogenously expressing NK$_1$ receptors are centrifuged and taken up in the incubation buffer containing 50 mM TRIS, 150 mM NaCl, 4 mM CaCl$_2$, protease inhibitors at ⅟₁₀₀$^e$ (Cocktail SIGMA P8340) and 0.2% BSA. The volume of incubation buffer is determined so as to obtain a concentration of 5×10$^6$ cells/ml. The cell preparation is then incubated together with 1.5 nM [$^3$H]-Substance P and the compound under test for 90 minutes at ambient temperature. Non-specific binding is determined in the presence of 1 μM GR 205171.

At the end of the incubation period, the samples ate filtered through Unifilter GF/B type filters pretreated with PEI (0.1%) and washed several times with the filtration buffer (50 nM TRIS, 150 mM NaCl, 4 mM CaCl$_2$). The radioactivity retained on the filters is measured by counting after addition of scintillation liquid to the filters. The counts are analysed by non-linear regression, allowing the isotherms to be plotted and the IC$_{50}$ values to be determined. The latter are converted into inhibition constants (K$_i$) by means of the Cheng-Prusoff equation:

$$K_i = IC_{50}/(1+L/K_D)$$

wherein L is the concentration of [$^3$H]-Substance P and KD is the dissociation constant of [$^3$H]-Substance P for human NK$_1$ receptors (0.53 nM). The results are expressed as pK$_i$ (−log K$_i$).

The results obtained for representative compounds of the invention are collated in the following table:

| Compound | pK$_i$ NK$_1$ |
|---|---|
| Example 1 | 8.47 |
| Example 2 | 7.74 |
| Example 3 | 6.79 |
| Example 5 | 6.40 |
| Example 11 | 6.31 |
| Example 79 | 6.29 |

EXAMPLE 221

Pharmaceutical Composition

Formula for the preparation of 1000 tablets each containing 10 mg of active ingredient:

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

The invention claimed is:

1. A compound selected from those of formula (I):

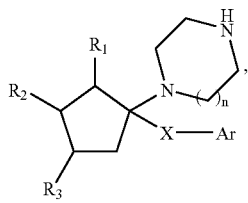

wherein:

$R_3$ represents a hydrogen atom, and $R_1$ and $R_2$ together with the carbon atoms carrying them form a benzene or naphthalene ring structure, each of the ring structures being optionally substituted by one or more identical or different substituents selected from hydrogen, halogen and linear or branched $C_1$-$C_6$alkyl optionally substituted by one or more halogen atoms, or $R_1$ represents a hydrogen atom, and $R_2$ and $R_3$ together with the carbon atoms carrying them form a benzene or naphthalene ring structure, each of the ring structures being optionally substituted by one or more identical or different substituents selected from hydrogen, halogen and linear or branched $C_1$-$C_6$alkyl optionally substituted by one or more halogen atoms, n represents 1 or 2, —X— represents a group selected from —(CH$_2$)$_m$—O—Ak-, —(CH$_2$)$_m$—NR$_4$-Ak-, —(CO)—NR$_4$-Ak- and —(CH$_2$)$_m$—NR$_4$—(CO)—, m represents an integer between 1 and 6 inclusive, Ak represents a linear or branched $C_1$-$C_6$alkylene chain optionally substituted by a hydroxy group, and $R_4$ represents a hydrogen atom, or linear or branched $C_1$-$C_6$alkyl group, Ar represents aryl or heteroaryl group, and its enantiomers, diastereoisomers, and addition salts thereof with a pharmaceutically acceptable acid, it being understood that:

an aryl group means phenyl, biphenylyl or naphthyl, each of those groups being optionally substituted by one or more identical or different groups selected from halogen, linear or branched $C_1$-$C_6$alkyl, linear or branched $C_1$-$C_6$alkoxy, hydroxy, cyano and linear or branched $C_1$-$C_6$trihaloalkyl, a heteroaryl group means thienyl or pyridyl, each of those groups being optionally substituted by one or more identical or different groups selected from halogen, linear or branched $C_1$-$C_6$alkyl, linear or branched $C_1$-$C_6$alkoxy, hydroxy and linear or branched $C_1$-$C_6$trihaloalkyl.

2. The compound of claim 1, wherein $R_1$ and $R_2$ together with the carbon atoms carrying them form an optionally substituted benzene ring and $R_3$ represents a hydrogen atom, or $R_2$ and $R_3$ together with the carbon atoms carrying them form an optionally substituted benzene ring and $R_1$ represents a hydrogen atom.

3. The compound of claim 1, wherein n represents 1.

4. The compound of claim 1, wherein m represents 1.

5. The compound of claim 1, wherein Ar represents an aryl group.

6. The compound of claim 1, selected from:

1-[(1RS)-1-(3,5-dibromobenzyloxymethyl)indan-1-yl]piperazine, its enantiomers, diastereoisomers, and addition salts thereof with a pharmaceutically acceptable acid, 1-[(1RS)-1-(3,5-dimethylbenzyloxymethyl)indan-1-yl]piperazine, its enantiomers, diastereoisomers, and addition salts thereof with a pharmaceutically acceptable acid, 1-[2-(3,5-dimethylbenzyloxymethyl)indan-2-yl]piperazine, and addition salts thereof with a pharmaceutically acceptable acid, N-[(3,5-bis(trifluoromethyl)benzyl]-2-(1-piperazinyl)-2-indancarboxamide, and addition salts thereof with a pharmaceutically acceptable acid, (1RS)-N-benzyl-N-methyl-1-(1-piperazinyl)-1-indancarboxamide, its enantiomers, diastereoisomers, and addition salts thereof with a pharmaceutically acceptable acid, (1RS)-N-[3,5-bis(trifluoromethyl)benzyl]-N-methyl-1-(1-piperazinyl)-1-indan-carboxamide, its enantiomers, diastereoisomers, and addition salts thereof with a pharmaceutically acceptable acid, (1RS)-N-(3,5-dimethylbenzyl)-1-(1-piperazinyl)-1-indancarboxamide, its enantiomers, diastereoisomers, and addition salts thereof with a pharmaceutically acceptable acid, N-(3,5-difluorobenzyl)-2-(1-piperazinyl)-2-indancarboxamide, and addition salts thereof with a pharmaceutically acceptable acid, N-(3,5-dichlorobenzyl)-N-methyl-2-(1-piperazinyl)-2-indancarboxamide, and addition salts thereof with a pharmaceutically acceptable acid, (1RS)-N-(3,5-difluorobenzyl)-N-methyl-1-(1-piperazinyl)-1-indancarboxamide, its enantiomers, diastereoisomers, and addition salts thereof with a pharmaceutically acceptable acid, (1RS)-N-[3-fluoro-5-(trifluoromethyl)benzyl]-N-methyl-1-(1-piperazinyl)-1-indan-carboxamide, its enantiomers, diastereoisomers, and addition salts thereof with a pharmaceutically acceptable acid, (1RS)-1-[1-(3,5-difluorobenzyloxymethyl)indan-1-yl]piperazine, its enantiomers, diastereoisomers, and addition salts thereof with a pharmaceutically acceptable acid, N-(3-chloro-5-fluorobenzyl)-N-methyl-2-(1-piperazinyl)-2-indancarboxamide, and addition salts thereof with a pharmaceutically acceptable acid, 1-[(1RS)-1-(3,5-difluorobenzyloxymethyl)indan-1-yl]piperazine, its enantiomers, diastereoisomers, and addition salts thereof with a pharmaceutically acceptable acid, (1RS)-N-(3,5-difluorobenzyl)-N-methyl-1-(1-piperazinyl)-1-indancarboxamide, its enantiomers, diastereoisomers, and addition salts thereof with a pharmaceutically acceptable acid, 1-[(1RS)-1-(3,5-difluorobenzyloxymethyl)-5,6-difluoroindan-1-yl]piperazine, its enantiomers, diasteroisomers, and addition salts thereof with a pharmaceutically acceptable acid, and 1-[(1RS)-1-(3-bromo-5-fluorobenzyloxymethyl)indan-1-yl]piperazine, its enantiomers, diasteroisomers, and addition salts thereof with a pharmaceutically acceptable acid, and enantiomers, diasteroisomers, and additional salts thereof with a pharmaceutically acceptable acid.

7. A pharmaceutical composition comprising as active ingredient a compound of claim 1, in combination with one or more pharmaceutically acceptable, inert, non-toxic carriers.

8. A method for treating a living animal body, including a human, afflicted with a condition selected from depressive states, comprising the step of administering to the living animal body, including a human, an amount of a compound of claim 1 which is effective for alleviation of the condition.

* * * * *